United States Patent [19]
Theodoridis

[11] Patent Number: 5,214,154
[45] Date of Patent: May 25, 1993

[54] HERBICIDAL ARYL TRIAZOLINONES

[75] Inventor: George Theodoridis, Princeton, N.J.

[73] Assignee: FMC Corporation, Philadelphia, Pa.

[21] Appl. No.: 942,695

[22] Filed: Sep. 9, 1992

Related U.S. Application Data

[60] Division of Ser. No. 708,966, May 31, 1991, Pat. No. 5,174,809, which is a division of Ser. No. 455,894, Dec. 28, 1989, Pat. No. 5,041,155, which is a continuation-in-part of Ser. No. 332,835, Apr. 3, 1989, abandoned, which is a continuation-in-part of Ser. No. 946,667, Dec. 31, 1986, Pat. No. 4,818,275, which is a continuation-in-part of Ser. No. 811,615, Dec. 20, 1985, abandoned.

[51] Int. Cl.$^5$ .................................. C07D 249/125
[52] U.S. Cl. .................................... 548/263.2
[58] Field of Search ................................ 548/263.2

[56] References Cited

U.S. PATENT DOCUMENTS

| | | | |
|---|---|---|---|
| 3,922,162 | 11/1975 | Krenzer | 548/263.2 |
| 4,398,943 | 8/1983 | Kajioka et al. | 71/92 |
| 4,404,019 | 9/1983 | Uematsu et al. | 71/92 |
| 4,919,708 | 4/1990 | Maravetz | 548/263.2 |

FOREIGN PATENT DOCUMENTS 60-136573 7/1985 Japan .................... 548/263.2

OTHER PUBLICATIONS

Chemical Abstracts 99: 175601t (1983).
Chemical Abstracts 103: 87884h (1983).
Chemical Abstracts 103: 104979n (1985).
Chemical Abstracts 103: 104980f (1985).
Chemical Abstracts 103: 104981g (1985).

*Primary Examiner*—Patricia L. Morris
*Attorney, Agent, or Firm*—Stanford M. Back; Robert M. Kennedy

[57] ABSTRACT

Herbicidal compounds of the formula

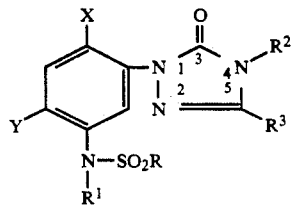

in which, for example, X is Br, Cl or F; Y is Cl or Br, $R^2$ is $CHF_2$, $R^3$ is $CH_3$, R is alkyl, dialkylamino, carboxymethyl, hydroxy, haloalkyl, or aryl, and $R^1$ is H, Na, lower alkyl or $-SO_2R$.

2 Claims, No Drawings

HERBICIDAL ARYL TRIAZOLINONES

This application is a division of U.S. application Ser. No. 708,966, filed May 31, 1991, now U.S. Pat. No. 5,174,809, which in turn is a division of U.S. application Ser. No. 455,894, filed Dec. 28, 1989, (now U.S. Pat. No. 5,041,155) which in turn is a continuation-in-part of U.S. application Ser. No. 332,835, filed Apr. 3, 1989, (now abandoned) which in turn is a continuation-in-part of U.S. application Ser. No. 946,667, filed Dec. 31, 1986, (now U.S. Pat. No. 4,818,275) which in turn is a continuation-in-part of U.S. application Ser. No. 811,615, filed Dec. 20, 1985, now abandoned.

The invention described in this application pertains to weed control in agriculture, horticulture, and other fields where there is a desire to control unwanted plant growth. More specifically, the present application describes certain herbicidal aryl triazolinones, compositions of them, methods of preparing them, and methods for preventing or destroying undesired plant growth by preemergence or postemergence application of the herbicidal compositions to the locus where control is desired. The present compounds may be used to effectively control a variety of both grassy and broadleaf plant species. The present invention is particularly useful in agriculture; a number of compounds described herein show a selectivity favorable to certain crops (e.g. soybeans on preemergence treatment) at application levels which inhibit the growth of or destroy a variety of weeds.

One aspect of this invention relates to herbicidal compounds of the general formula

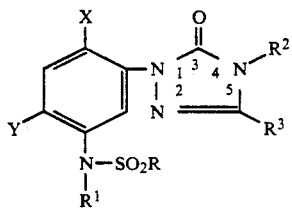

(Formula I)

wherein

X is bromine, chlorine, fluorine, alkyl (e.g. $CH_3$), or haloalkyl (e.g. $CF_3$);

Y is bromine, chlorine, fluorine, methyl, haloalkyl (e.g. $CH_2F$ or $CF_3$), nitro, a radical of the formula $R^8OCH_2$—, $R^8SCH_2$—, $R^8SOCH_2$—or $R^8SO_2CH_2$— where $R^8$ is $C_1$—$C_3$alkyl, $C_2$—$C_5$alkenyl, or $C_3$—$C_5$ alkynyl (e.g., $CH_3OCH_2$—, $CH_3SCH_2$—, $CH_2$=$CHCH_2OCH_2$—$CH_2$=$CHCH_2SCH_2$—, CH=$CCH_2SCH_2$—); $R^8$ may also be phenyl (or phenyl substituted with e.g., halogen, alkyl, haloalkyl), $R^3$ may be halogen (e.g. chlorine), alkyl (e.g. of 1 to 5 carbon atoms), haloalkyl (e.g. of 1 to 5 carbon atoms such as difluoromethyl), alkoxyalkyl (e.g. of 2 to 6 carbon atoms such as methoxymethyl), cyanoalkyl (e.g. of 2 to 6 carbon atoms such as cyanomethyl), arylalkyl such as benzyl, alkylthio (e.g. of 1 to 3 carbon atoms such as methylthio) or the corresponding alkylsulfinyl or alkylsulfonyl, or alkylthioalkyl (e.g., of 1 to 3 carbon atoms independently with respect to each alkyl, such as methylthiomethyl) or the corresponding alkylsulfinylalkyl or alkylsulfonylalkyl;

$R^2$ may be alkyl (e.g. of 1 to 5 carbon atoms), lower alkoxy (e.g. methoxy), haloalkyl (e.g. to 1 to 5 carbon atoms, such as $CHF_2$, $CF_2CHF_2$, or $CH_2CH_2CH_2F$), alkenyl of 2 to 5 carbon atoms (e.g. allyl), alkynyl of 3 to 5 carbon atoms (e.g. propargyl), cyanoalkyl (e.g. $CH_2CN$ or $CH_2CH_2CN$), thiocyanoalkyl (e.g. $CH_2SCN$) or a group of the formula -alkylene-$Y^1$-$R^5$ in which said alkylene group (e.g. —$CH_2$—) has 1 to 5 carbon atoms, $Y^1$ being oxygen or $S(O)r$ in which r is 0 to 2, and $R^5$ being alkyl (e.g. of 1 to 5 carbon atoms such as methyl), alkenyl of 2 to 5 carbon atoms (e.g. allyl) or alkynyl of 3 to 5 carbon atoms (such as propargyl);

R may be alkyl (such as straight chain or branched chain lower alkyl, e.g. methyl, ethyl, propyl), haloalkyl (such as $CF_3$ or $CHF_2$), dialkylamino, carboxymethyl, hydroxy, or aryl (such as phenyl, optionally substituted with one or more of: halogen such as Cl, Br or F; alkyl such as lower alkyl, e.g. methyl; alkoxy such as lower alkoxy, e.g. methoxy; cyano; cyanomethyl; nitro; amino; arylamino such as phenylamino; mono- and dialkylamino such as methylamino or dimethylamino; carboxyl; alkoxycarbonyl such as —$COOC_2H_5$; alkoxyalkyl such as alkoxymethyl of 2 to 4 carbon atoms; alkoxycarbonylalkyl such as —$CH_2COOC_2H_5$; benzyl; or hydroxy).

$R^1$ may be hydrogen, alkyl (e.g. straight or branched chain lower alkyl such as methyl, ethyl, propyl, isopropyl or butyl), benzyl, haloalkyl (e.g. $CHF_2$ or $CH_2CH_2CH_2F$), alkoxy (e.g. methoxy), $SO_2R$, alkynyl (such as propargyl), alkenyl (such as allyl), a group of formula -alkylene-$SO_2R$ (in which, for example, said alkylene group (e.g. —$CH_2$—) has 1 to 4 carbon atoms, alkoxymethyl (such as methoxymethyl), cyanomethyl, carboxymethyl (including salts thereof) or alkoxycarbonylmethyl (e.g. ethoxycarbonylmethyl); or R and $R^1$ together may be a divalent radical such as alkylene (e.q. of 1 to 10 carbon atoms such as methylene or 1,3-propylene).

$R^1$ may also be a salt-forming group such as a metal (e.g. Na, K or Ca) or ammonium (e.g. NH4 or lower alkylsubstituted ammonium) or sulfonium or sulfoxonium (such as salts or bases of the formula $R''_3S(O)_n$ where R" is, for instance, lower alkyl (e.q. $C_{1-3}$ alkyl) and n is zero or one, e.g. the trimethylsulfoxonium salt.

In each aspect of the invention, it is often preferable that any alkyl, alkenyl, alkynyl or alkylene radical have less than 6 carbon atoms.

Representative compounds according to the invention are shown in Table 1 below.

The compounds of this invention are preferably those whose Methoxy Analog or Propargyloxy Analog is a herbicide. The term "Methoxy Analog" is used here to designate a compound which is otherwise identical except that it has a methoxy group instead of the —$N(R^1)SO_2R$ group of said compound. The term "Propargyloxy Analog" is similarly used here for a compound which is otherwise identical except that it has a propargyloxy group instead of the —$N(R^1)SO_2R$ group of said compound.

The compounds of this invention preferably have Methoxy Analogs and Propargyloxy Analogs of marked herbicidal properties. For instance said Analogs of the preferred compounds show at least 50% kill of at least one of the following species of plants when applied under at least one of the following modes at the rate of 0.5 kg/ha, and more preferably show such kill of at least 50% when applied at the rate of 0.1 kg/ha: Species: velvetleaf (*Abutilon theoohrasti*), green foxtail (*Setaria viridis*); Modes: pre-emergent, post-emergent. Testing for such herbicidal activity may be carried out in the manner described below (under the heading "Herbicidal Activity").

An additional aspect of the present invention pertains to the discovery that the herbicidal compounds of the invention also have fungicidal properties. Thus, use of the present compounds as herbicides give the incidental benefit of fungus disease control, prevention or moderation, particularly with respect to rice blast. Compound 1 of Table 1 is a preferred embodiment for this aspect of the invention.

Compound 1 gave 42% and 34% rice blast control at application rates of 0.0078 kg/ha and 0.002 kg/ha respectively; rice plant injury (phytotoxicity) at the 0.0078 kg/ha application rate was 20%, and at the 0.002 kg/ha rate was 7%. The testing procedure is given below under the heading "Rice Blast Testing Procedure".

The compounds of this invention may be prepared by the use of steps generally described in the literature or by methods analogous or similar thereto and within the skill of the art. In the Examples below an arylamine is treated to form the corresponding aryl hydrazine whose hydrazine portion is then modified to form a triazolinone ring. Thereafter the benzene ring of the intermediate is nitrated, the nitro group is reduced to form an amino group, which is then treated with $RSO_2Cl$ or $(RSO_2)_2$ to convert it to an $-N(R^1SO_2R$ group (e.g. by using a weak base such as pyridine, as in Example 19 below, or $NaHCO_3$) or to an $-N(SO_2R)_2$ group (as in Examples 2, 5, 9, 12, 14, or 17). The compound having the $-N(SO_2R)_2$ group may then be treated (as with a base such as NaOH) to form the corresponding $-N(R^1)SO_2R$ group, where $R^1$ is a salt-forming group (e.g. Na); this may then be treated with an acid to form the corresponding (acidic) $-NHSO_2R$ group. Subsequent alkylation (as by treatment with the appropriate alkyl halide as in Example 7) forms the corresponding $-N(R^1)SO_2R$ group; $R^1$ substituents other than alkyl may be introduced similarly, in known manner. When the reaction sequence involves $RSO_2Cl$ treatment of an intermediate having hydrogen on the 4-nitrogen of the triazolinone ring, that hydrogen may also be replaced, during such treatment, by $RSO_2-$ to form an intermediate (such as compound 36 in Table 1 below, which has 3 $RSO_2-$ groups) from which the $RSO_2-$ group on said 4-nitrogen may be removed readily by the treatment with the base, after which the appropriate $R^2$ group may be substituted on said 4-nitrogen.

In the Examples the modification of the hydrazine group to form a triazolinone ring is effected by reaction with pyruvic acid (forming the hydrazone) and then with a phosphoryl azide. Other techniques for this include treating the substituted phenylhydrazine with any of the following four types of reagents:

(a) an inner salt of a 3-(i-iminoalkylmercapto)-1propanesulfonic acid (which may be prepared according to Reid and Schmidt, Ann. Chem., 676, 114 (1964) from 1,3-propanesultone and a thioamide), to form an amidrazone followed by reaction with a source of phosgene, as by the following reaction sequence (which is also illustrated in Example 15 below),

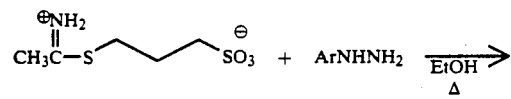

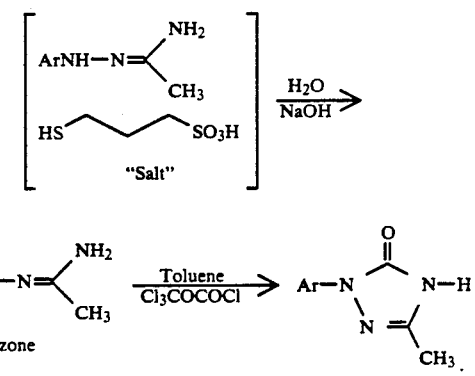

in which "Ar" is aromatic as described below.

(b) An imidate ester of the formula

to form the corresponding amidrazone (as described, for instance, in the article by Neilson et al. "The Chemistry of Amidrazones", Chem. Rev. 70, 151(1970) at page 156), followed by reaction with a source of phosgene, as in (a) above, Rc and Rd being alkyl or other suitable radical.

(c) A compound of the formula

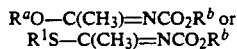

(where $R^a$ and $R^b$ are lower alkyl) in the presence of a base according to the following sequence:

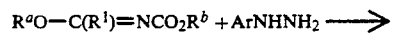

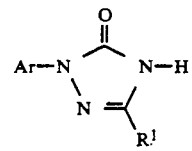

in which $R^1$ is defined above, e.g. methyl;

(d) A haloalkylnitrile (e.g. a fluoroalkyl, fluorochloroalkyl or fluorobromoalkyl nitrile such as $ClCF_2CN$, followed by reaction with a source of phosgene, so that the reaction may proceed along the following lines, for instance to form the aryl 3-haloalkyl triazoline, thus:

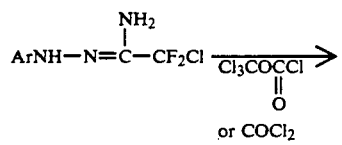

or $COCl_2$

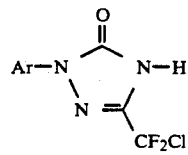

In Examples 1, 8 and 13 below two halogen substituents are present on the "Ar" portion of the molecule before the triazoline ring is formed; that is, the Ar portion of the aryl hydrazine has halo substituents at its 2 and 4 positions. Instead, in each of the processes illustrated above (and in the process of those Examples 1, 8, and 13) one or both of the halogens may be placed on Ar after the triazoline ring is formed. Thus, the Ar group of the arylamine (and of the corresponding hydrazine formed therefrom) may be phenyl or monohalophenyl (e.g. 2-fluorophenyl) or nitrophenyl (e.g. 3-nitrophenyl) or monohalonitrophenyl (e.g. 2-fluoro-5-nitrophenyl) and the aryl triazoline formed therefrom may then be treated to (a) alkylate the nitrogen at the 4-position of the triazoline ring (in known manner, e.g. with an alkyl or fluoroalkyl halide, such as with ClCHF2 at a temperature of, say, 20 to 150° C.) to add the preferred CHF2 substituent and (b) to introduce additional substituents onto the aromatic ring, as by halogenation with chlorine or bromine (e.g. by reacting with $Cl_2$, $Br_2$ or $SO_2Cl_2$ at a temperature of, say, 20° to 150° C.). For instance, the alkylation of the nitrogen at the 4-position may be effected first, after which the nitro group (if present) may be reduced to an amino group in conventional manner, the amino group may be converted to the organic sulfonylamino group (e.g. in the manner shown in the Examples using, for instance, a temperature below 60° C. such as -10° to 50° C. in the presence of a suitable base and an inert solvent), after which the compound may be halogenated as indicated above to place the halogen substituent or substituents on its benzene ring. For instance, for making one preferred class of compounds of the invention in which the benzene ring has a 2-fluoro substituent, the starting material may be 2-fluoro-5-nitrophenylhydrazine, which may be treated as described above to produce successively a series of intermediates such as:

1-(2-fluoro-5-nitrophenyl)-4,5-dihydro-3-methyl1,2,4-triazol-5(1H)-one, then 1-(2-fluoro-5-nitrophenyl)-4,5-dihydro-4-difluoro-methyl-3-methyl-1,2,4-triazol-5(1H)-one, 1-(2-fluoro-5-aminophenyl)-4,5-dihydro-4-difluoro-methyl-3-methyl-1,2,4-triazol-5(1H)-o the corresponding compound having an —N(R$^1$-)SO$_2$R group at the 5-position of the benzene ring such as 1-[2-fluoro-5-(N-ethylsulfonyl)aminophenyl]-4,5-dihydro-3-methyl-1,2,4-triazol-5(1 followed by halogenation to place, for instance, a chloro or bromo substituent at the 4-position of the benzene ring.

Instead of alkylating at the 4-position of the triazoline ring at an early stage, e.g. prior to altering the nitro group, this alkylation step may be delayed until after the above-described halogenation of the benzene ring.

Another series of intermediates comprises:

1-(5-nitrophenyl)-4,5-dihydro-3-methyl-1,2,4-triazol-5(1H)-one, then 1-(5-nitrophenyl)-4,5-dihydro-4-difluoromethyl-3-methyl-1,2,4-triazol-5(1H)-one, then 1-(5-aminophenyl)-4,5-dihydro-4-difluoromethyl-3-methyl-1,2,4-triazol-5(1H)-one, then the corresponding compound having an -N(R$^1$)SO$_2$R group at a meta-position on the benzene ring such as 1-[5-(N-ethylsulfonyl)aminophenyl]-4,5-dihydro-4-difluoro-methyl-3-methyl-1,2,4-triazol-5(1H)-one, followed by halogenation to place, for instance, two chloro (or bromo) substituents at the 2- and 4-positions of the benzene ring.

Variations in the sequence in which the reactions are carried out will produce other intermediates such as:

1-(2-chloro-5-nitrophenyl)-4,5-dihydro-4-difluoro-methyl-3-methyl-1,2,4-triazol-5(1H)-one, w converted to the corresponding 2-fluoro-5-nitrophenyl compound by appropriate treatment with KF to replace the 2-chloro substituent by a 2-fluoro substituent;

also, 1-(2-fluorophenyl)-4,5-dihydro-3-methyl-1,2,4-triazol-5(1H)-one, which may be converted to 1-(2-fluorophenyl)-4,5-dihydro-4-difluoromethyl-3-methyl-1,2,4-triazol-5(1H)-one which may then be chlorinated, as by appropriate treatment with SO$_2$Cl$_2$, to give the corresponding 2-fluoro-4-chlorophenyl compound.

Another sequence involves formation of:

2-fluoro-4-nitrophenylhydrazine, then 1-(2-fluoro-4-nitrophenyl)-4,5-dihydro-3-methyl,2,4-triazol-5(1H)-one, then 1-(2-fluoro-4-nitrophenyl)-4,5-dihydro-4-difluoro-methyl-3-methyl-1,2,4-triazol-5(1H)-one, t 1-(2-fluoro-4-aminophenyl)-4,5-dihydro-4-difluoro-methyl-3-methyl-1,2,4-triazol-5(1H)-treatment to replace the amino group by chlorine (as by treatment with NaN02/HCl and then CuCl).

Similarly, when the reagent(s) used to react with the aryl hydrazine are such as to produce a triazolinone having a haloalkyl (e.g. CHF2) group instead of an alkyl group on the carbon at the 3-position of the heterocyclic ring, the series of intermediates may include, successively (from 2-fluoro-5-nitrophenylamine, and then its hydrazine) such compounds as:

l-(2-fluoro-5-nitrophenyl)-4,5-dihydro-3-difluoro-methyl-1,2,4-triazol-5(1H)-one, then 1-(2-fluoro-5-nitrophenyl)-4,5-dihydro-4-methyl (or difluoromethyl)-3-difluoromethyl-1,2,4-triazol-5(1H)one, then 1-(2-fluoro-5-aminophenyl)-4,5-dihydro-4-methyl (or difluoromethyl)-3-difluoromethyl-1,2,4-triazol-5(1H)one, then the corresponding compound having an -N(R$^1$)SO$_2$R group at the 5-position of the benzene ring such as 1-[2-fluoro-5-(N-ethylsulfonyl)aminophenyl]-4,5-dihydro-4-methyl (or difluoromethyl)-3-difluoromethy 1,2,4-triazol-5(1H)-one, followed by halogenation to place, for instance, a chloro or bromo substituent at the 4-position of the benzene ring.

Another series of intermediates, from 5-nitrophenylamine includes:

1-(5-nitrophenyl)-4,5-dihydro-3-difluoromethyl1,2,4-triazol-5(1H)-one, then 1-(5-nitrophenyl)-4,5-dihydro-4-methyl (or difluoromethyl)-3-difluoromethy 1,2,4-triazol-5(1H)-one, then 1-(5-aminophenyl)-4,5-dihydro-4-methyl (or difluoromethyl)-3-difluoromethyl-1,2,4-triazol-5(1H)-o the corresponding compound having an -N(Rl)SO$_2$R group at a meta-position on the benzene ring such as 1-[5-(N-ethylsulfonyl)aminophenyl]-4,5-dihydro-4methyl or difluoromethyl)-3-difluoromethyl-1,2,4-triazol-5(1H)-one, followed by halogenation to place, for instance, two chloro (or bromo) substituents at the 2- and 4-positions of the benzene ring.

Variations in the sequence in which the reactions are carried out will pro duce other intermediates such as:

1-(2-chloro-5-nitrophenyl)-4,5-dihydro-4-(methyl or difluoromethyl)-3-difluoromethyl-1,2,4-triazol-5(1H)-one, which may be converted to the corresponding 2-fluoro-5-nitrophenyl compound by appropriate treatment with KF to replace the 2-chloro substituent by a 2-fluoro substituent;

also, 1-(2-fluorophenyl)-4,5-dihydro-3-difluoro-methyl-1,2,4-triazol-5(1H)-one, which may be conve to 1-(2-fluorophenyl)-4,5-dihydro-4-methyl (or difluoromethyl)-3-methyl-1,2,4-triazol-5(1H)-one Which may then be chlorinated, as by appropriate treatment with $SO_2Cl_2$ to the corresponding 2-fluoro-4-chlorophenyl compound.

Another sequence involves formation of:

2-fluoro-4-nitrophenylhydrazine, then 1-(2-fluoro-4-nitrophenyl)-4,5-dihydro-3-difluoromethyl-1,2,4-triazol-5(1H)-one, then 1-(2-fluoro-4-nitrophenyl)-4,5-dihydro-4-methyl (or difluoromethyl)-3-difluoromethyl-1,2,4-triazol-5(1H)one, then 1-(2-fluoro-4-aminophenyl)-4,5-dihydro-4-methyl (or difluoromethyl)-3-difluoromethyl-1,2,4-triazol-5(1H)one, followed by treatment to replace the amino group by a chlorine (as by treatment with $NaNO_2$/HCl and then CuCl).

Alternatively, one may start with 4-fluoronitrobenzene and, by a series of reactions (e.g. by reducing the $NO_2$ group to an amino group and then nitrating to form 3-nitro-4-fluoroaniline, followed by treatment with the alkylsulfonyl halide), form 2-fluoro-5-bis(N-ethylsulfonylamino)nitrobenzene, which is then reduced to form 2-fluoro-5-bis(N-ethylsulfonyl)amino aniline and then converted to the corresponding 1-[2-fluoro-5-bis(N' ethylsulfonyl)aminophenyl]-3-methyl-$\Delta^2$-1,2,4-triazolin 5-one, which may then be treated to substitute an $R^2$ group on the triazolinone ring.

From 2-fluoro-5-nitroaniline one may (as illustrated in Example 20) acetylate the $NH_2$ to protect it; then reduce the nitro group to form an amino group; chlorinate and treat with alkylsulfonyl chloride in any order (to form, e.g., 2-fluoro-4-chloro-5-(ethylsulfonylamino)acetanilide); then hydrolyze off the acetyl group to form 2-fluoro-4-chloro-5-(ethylsulfonylamino) aniline, whose free $NH_2$ group may then be converted (e.g. as discussed above) to a triazolinone ring.

Similarly, starting with 2-fluoro-4-chloro-5-nitroaniline one may acetylate to form 2-fluoro-4-chloro-5nitroacetanilide (m.p. 138°-140° C.); reduce to form 2-fluoro-4-chloro-5-aminoacetanilide (m.p. 117-120° dec.) and then alkylsulfonate to form, e.g. 2-fluoro-4-chloro-5-bis(N-ethylsulfonylamino)acetanilide (m.p. 218°-219° C.) and/or 2-fluoro-4-chloro-5-(N-ethylsulfonylamino)acetanilide, which may be treated to hydrolyze off the acetyl group and then converted to a triazolinone as discussed above.

The following Examples illustrate the preparation of the compounds of this invention. In those Examples the heterocyclic ring is described as: a2-1,2,4-triazolin5-one: that is a synonym for: dihydro-1,2,4-triazol5(1H)-one.

EXAMPLE 1

SYNTHESIS OF 1-(5-AMINO-4-CHLORO-2-FLUORO-PHENYL)-3-METHYL-4-DIFLUOROMETHYL-$\Delta^2$-1,2,4-TRIAZOLIN-5-ONE AS AN INTERMEDIATE

Step A

Synthesis of 2-Fluoroacetanilide as an Intermediate

To a stirred solution of 100 g (0.9 mole) of 2-fluoroaniline in 200 ml of water was added 105 ml (1.1 moles) of acetic anhydride. Upon completion of addition the reaction mixture was filtered to collect a solid. The solid was dried to yield 105 g of 2-fluoroacetanilide; m.p. 74°-76° C. The reaction was repeated several times.

Step B

Synthesis of 4-Chloro-2-fluoroacetanilide as an Intermediate

To a stirred solution of 180.0 g (1.17 moles) of 2-fluoroacetanilide in 210 ml of p-dioxane was slowly added dropwise 173.4 g (9.29 moles) of sulfuryl chloride. Upon completion of addition the reaction mixture stirred at ambient temperature for 16 hours. A solid was collected by filtration, washed with water, and dried to yield 155 g of 4-chloro-2-fluoroacetanilide; m.p. 147°-148° C.

Step C

Synthesis of 4-Chloro-2-fluoroaniline as an Intermediate

To a stirred solution of 155 g (0.83 mole) of 4-chloro-2-fluoroacetanilide in 400 ml of ethanol was added dropwise a solution of 72.0 g (1.8 moles) of sodium hydroxide in 100 ml of water. Upon completion of addition the reaction mixture was heated under reflux for three hours. The reaction mixture was cooled to ambient temperature and extracted with diethyl ether. The combined extracts were concentrated under reduced pressure to a residual oil. The oil was distilled under reduced pressure to yield 81.0 g of 4-chloro-2-fluoroaniline; b.p. 83-85/12 mm. The reaction was repeated several times.

Step D

Synthesis of Pyruvic Acid, 4-chloro-2-fluorophenylhydrazone as an Intermediate

Under a nitrogen atmosphere, a stirred solution of 20.0 g (0.137 mole) of 4-chloro-2-fluoroaniline in 162 ml of concentrated hydrochloric acid was cooled to −9° C. and a solution of 9.5 g (0.137 mole) of sodium nitrite in 50 ml of water was added dropwise at a rate to maintain the reaction mixture temperature at −9° C. The complete addition required 30 minutes. The reaction mixture was stirred for an additional one hour at −9° C. to 0° C., then a solution of 68.1 g (0.30 mole) of stannous chloride in 68 ml of concentrated hydrochloric acid was added dropwise at a rate to maintain the reaction mixture temperature at −9° C. to 0° C. The complete addition required 40 minutes. The reaction mixture stirred at −9° C. to 0° C. for an additional 30 minutes, then was allowed to warm to ambient temperature where it stirred for two hours. Water, 110 ml, was added to the reaction mixture, and then a solution of 12.2 g (0.137 mole) of pyruvic acid in 125 ml of water was added dropwise during a five minute period. Upon completion of addition the reaction mixture stirred an additional 30 minutes then was filtered to collect a solid. The solid was washed with water and dried to give 27.7 g of pyruvic acid, 4-chloro-2-fluorophenylhydrazone; m.p. 162°–163° C. The reaction was repeated several times.

Step E

Synthesis of
1-(4-chloro-2-fluorophenyl)-3-methyl-$\Delta^2$-1,2,4-triazolin-5-one as an Intermediate To a stirred suspension of 25.4 g (0.110 mole) of pyruvic acid, 4-chloro-2-fluorophenylhydrazone in 200 ml of toluene was added 11.1 g (0.11 mole) of triethylamine. The reaction mixture became homogeneous and 30.3 g (0.11 mole) of diphenylphosphoryl azide was added. Upon completion of addition the reaction mixture was heated to reflux where it stirred for two hours. The reaction mixture was cooled to ambient temperature and extracted with 300 ml of aqueous 1N sodium hydroxide. The extract was neutralized with concentrated hydrochloric acid and a solid precipitate collected by filtration. The solid was washed with water and dried to yield 21.1 g of 1-(4-chloro-2-fluorophenyl)-3-methyl-$\Delta^2$-1,2,4-tria-zolin-5-one; m.p. 189°–191° C. repeated several times.

Step F

Synthesis of
1-(4-chloro-2-luorophenyl)-3-methyl-4-difluoromethyl-$\Delta^2$-1,2,4-tria-zolin-5-one as an Intermediate A stirred solution of 27.4 g (0.12 mole) of 1-(4-chloro-2-fluorophenyl)-3-methyl-$\Delta^2$-1,2,4-tria-zolin-5-one, 13.5 g (0.24 mole) of hydroxide, and 3.9 g (0.012 mole) of tetrabutylammonium bromide in 500 ml of tetrahydrofuran was cooled in an ice bath and chlorodifluoromethane was bubbled into the reaction mixture. The ice bath was removed and chlorodifluoromethane continued to bubble into the reaction mixture until condensation of it was observed on a dry ice condenser attached to the reaction vessel. Upon completion of addition the reaction mixture stirred at ambient temperature for 16 hours. An additional 6.7 g (0.12 mole) of powdered potassium hydroxide was added to the reaction mixture and it was again saturated with chlorodifluoromethane. The reaction mixture was stirred for two hours then diluted with water. The mixture was extracted with diethyl ether and the combined extracts washed with water. The organic layer was dried with sodium sulfate and filtered. The filtrate was concentrated under reduced pressure to a residue. The residue was dissolved in methylene chloride and passed through a pad of silica gel. The eluate was concentrated under reduced pressure to a residual solid. The solid was recrystallized from methylene chloride-heptane to yield 9.5 g of 1-(4-chloro-2-fluorophenyl)-3-methyl-4-difluoro-methyl-$\Delta^2$-2-1,2,4-triazolin-5-one reaction was repeated several times.

Step G

Synthesis of
1-(4-chloro-2-fluoro-5-nitro-phenyl)-3-methyl-4-difluoromethyl-$\Delta^2$0 1,2,4-triazolin-5-one as an Intermediate To a stirred solution of 6.1 g (0.022 mole) of 1-(4-chloro-2-fluorophenyl)-3-methyl-4-difluoromethyl-$\Delta^2$-1,2,4-triazolin-5-one in 9 m sulfuric acid was slowly added 1.96 ml of 70% nitric acid, while maintaining the reaction mixture temperature at 25° C. Upon completion of addition the reaction mixture was stirred at 25° C. for 30 minutes, then poured into ice water. The resultant solid was collected by filtration. The solid was dissolved in methylene chloride and passed through a pad of silica gel. The eluate was subjected to column chromatography on silica gel. Elution was completed using 1:1-petroleum ether:methylene chloride. The appropriate fractions were combined and concentrated under reduced pressure to yield 3.0 g of 1-(4-chloro-2-fluoro-5-nitrophenyl)-3-methyl-4-difluoromethyl-$\Delta$1,2,4-triazolin-5-one; m.p. 102°–104° C. The reaction was repeated several times.

Step H

Synthesis of
1-(4-amino-4-chloro-2-fluoro-phenyl)-3-methyl-4-difluoromethyl-$\Delta^2$-1,2,4-triazolin-5-one as an Intermediate To a stirred solution of 4.0 g 0. 12 mole) of 1-(4-chloro-2-fluoro-5-nitrophenyl)-3-methyl-4-difluoromethyl-$\Delta^2$-1,2,4-triazolin-5-one in 50 ml of acetic acid and 20 ml of water was added portionwise 4.0 g (0.072 mole) of powdered iron at a rate to maintain the reaction mixture temperature below 35° C. Upon completion of addition the reaction mixture stirred at 25°–30° C. for two hours. The reaction mixture was diluted with diethyl ether with stirring, then was filtered through diatomaceous earth. The stirred filtrate was made basic with aqueous 10% sodium bicarbonate solution and solid potassium carbonate. The organic layer was separated, washed with three portions of water, then dried with sodium sulfate. The mixture was filtered and the filtrate concentrated under reduced pressure to a residue. The residue was purified by column chromatography on silica gel using methylene chloride:acetone as an eluent. The appropriate fractions were combined and concentrated under reduced pressure to yield 3.1 g of 1-(5-amino-4-chloro-2-fluorophenyl)-3-methyl-4-di-fluoromethyl-$\Delta^2$- 1,2,4-triazolin-5-one; m.p. 128°–129° C. The nmr and the ir spectra were consistent with the proposed structure. The reaction was repeated several times.

EXAMPLE 2

SYNTHESIS OF
1-[4-CHLORO-2-FLUORO-5-[BIS(N-METHYL-SULFONYL)AMINO]PHENYL]-3-METHYL-4-DIFLUOROMETHYL-$\Delta^2$-1,2,4-TRIAZOLIN-5-ONE (COMPOUND 24)

A stirred solution of 1.0 g (0.003 mole) of 1-(5-amino-4-chloro-2-fluorophenyl)-3-methyl-4-di-fluoromethyl-$\Delta^2$-1,2,4-triazolin-5-o in Example 1) and 0.76 g (0.008 mole) of triethylamine in 20 ml of methylene chloride was cooled in an ice/ acetone bath and 0.83 g (0.007 mole) of methanesulfonyl chloride was added dropwise at a rate to maintain the reaction mixture temperature below 0° C. The complete addition required five minutes. Upon completion of addition the reaction mixture was allowed to warm to ambient temperature where it stirred for 16 hours. After this time the reaction mixture was concentrated under reduced pressure to a residue. The residue was purified by column chromatography on silica gel using 50:1-methylene chlorideacetone as an eluent. The appropriate fractions were combined and concentrated under reduced pressure to a solid. The solid was recrystallized from acetone/heptane to yield 1.4 g of 1-[4-chloro-2-fluoro-5-[bis(N-methylsul-fonyl)amino]phenyl]-3-methyl-4-difluoromethy -triazolin-5-one; m.p. 180°–195° C.

The nmr and the ir spectra were consistent with the proposed structure.

Analysis calc'd for $C_{12}H_{12}ClF_3N_4O_5S_2$: C32.11; H 2.69; N12.48

Found: C 31.98; H 2.32; N 12.15.

EXAMPLE 3

SYNTHESIS OF 1-[4-CHLORO-2-FLUORO-5-(N-METHYLSUL-FONYL]AMINO)PHENYL]-3-METHYL-4-DIFLUOROMETHYL $\Delta^2$-1,2,4-TRIAZOLIN-5-ONE (COMPOUND 3)

To a stirred solution of 1.0 g (0.002 mole) of 1-[4-chloro-2-fluoro-5-[bis(N-methylsulfonyl)amino]

Phenyl]-3-methyl-4-difluormethyl-$\Delta^2$-1,2,4-tria-zolin-5-one (prepared as in Example 2) in 25 ml methanol was added a solution of 0.17 g (0.004 mole) of sodium hydroxide in 3 ml of water. Upon completion of addition the reaction mixture was stirred for 15 minutes then poured into 100 ml of water. The mixture was neutralized with concentrated hydrochloric acid and the solid precipitate collected by filtration. The solid was dried to yield 0.65 g of 1-[4-chloro-2-fluoro-5-(N-methylsulfonylamino)phenyl]-3-methyl-fluoromethyl-$\Delta^2$-1,2,4-triazolin-5-one; m.p. 156°–59° C.

The nmr spectrum was consistent with the proposed structure.

Analysis calc'd for $C_{11}H_{10}ClF_3N_4O_3S$:C 34.79; H 2.65; N 14.75;

Found: C 35.47; H 2.53; N 14.94.

EXAMPLE 4

SYNTHESIS OF 1-[4-CHLORO-2-FLUORO-5-[(N-ETHYL SULFONYL-N-METHYLSULFONYL)AMINO]-PHENYL]-3-METHYL-4-DIFLUOROMETHYL-$\Delta^2$-1,2,4-TRIAZOLIN-5-ONE (COMPOUND 28)

This compound was prepared in a manner analogous to that of Example 2, using 0.31 g (0.0009 mole) of 1-[4-chloro-2-fluoro-5-(N-methylsulfonylamino)-phenyl]-3-methyl-4-difluormethyl-$\Delta^2$-1,2,4  0.14 g (0.0011 mole) of ethanesulfonyl chloride, and 0.12 g of triethylamine in 5 ml of methylene chloride. The yield of 1-[4-chloro-2-fluoro-5-(N-ethyl-sulfonyl-N-methyl-sulfonyl)amino]phenyl]-3-methyl-4-difluoromethyl-$\Delta^2$-1,2,4-triazolin-5-one was 0.33 g; m.p. 128°–131.5° C.

The nmr spectrum was consistent with the proposed structure.

Analysis calc'd for $C_{13}H_{14}ClF_3N_4O_5S_2$: C 33.73; H3.05; N 12.11;

Found: C 33.57; H 3.17; N 12.

EXAMPLE 5

SYNTHESIS OF 1-[4-CHLORO-2-FLUORO-5-[BIS(N-ETHYLSUL-FONYL)AMINO]PHENYL]-3-METHYL-4-DI-FLUOROMETHYL-$\Delta^2$-1,2,4-TRIAZOLIN-5-ONE (COMPOUND 38)

This compound was prepared in a manner analogous to that of Example 2 using 1.0 g (0.003 mole) of 1-(5-amino-4-chloro-2-fluorophenyl)-3-methyl-4-difluoromethyl-$\Delta^2$-1,2,4-triazolin-5-o in Example 1) 0.9 g (0.007 mole) of ethanesulfonyl chloride and 0.7 g (0.007 mole) of triethylamine in methylene chloride. The yield of 1-[4-chloro-2-fluoro-5-[bis(N-ethylsulfonyl)amino]-phenyl]-3-methyl-4-difluoromethyl-$\Delta^2$-1,2,4-triazolin-5-one wa m.p. 143°-144° C.

The nmr spectrum was consistent with the proposed structure.

The reaction was repeated several times.

EXAMPLE 6

SYNTHESIS OF 1-[4-CHLORO-2-FLUORO-5-(N-ETHYL SULFONYLAMINO)PHENYL]-3-METHYL-4-DIFLUORO METHYL-$\Delta^2$-1,2,4-TRIAZOLIN-5-ONE (COMPOUND 11)

This compound was prepared in a manner analogous to that of Example 3, using 1.1 g (0.0022 mole) of -[4-chloro-2-fluoro-5-[bis(N-ethylsulfonyl)amino]phenyl]-3-methyl-4-difluoromethyl-$\Delta^2$-1,2,4-tria-zolin-5-one (prepared as in Example 5) and 0.17 g (0.0044 mole) of sodium hydroxide in 25 ml of methanol. The yield of 1-[4-chloro-2-fluoro-5-(Nethylsulfonylamino)phenyl]-3-methyl-4-difluoromethyl-$\Delta^2$1,2,4-triazolin-5-one was 0.8 g; m.p. 162°-163° C.

The nmr spectrum was consistent with the proposed structure.

Analysis calc'd for $C_{12}H_{12}ClF_3N_4O_3S$:C 37.46; H 3.14; N 14.56;

Found: C 37.65; H 3.12; N 14.44.

EXAMPLE 6A

SYNTHESIS OF 1-[4-CHLORO-2-FLUORO-5-(N-ETHYLSUL-FONYLAMINO)PHENYL]-3-METHYL-4-DIFLUOROMETHYL-$\Delta^2$-1,2,4-TRIAZOLIN-5-ONE (COMPOUND 11)

A stirred suspension of 1.0 g (0.0034 mole) of 1-(4-amino-4-chloro-2-fluorophenyl)-3-methyl-4-difluoromethyl-$\Delta^2$-1,2,4-triazqlin-5-one in 5 ml of methylene chloride was cooled in an ice water bath and 0.3 ml (0.0037 mole) of pyridine was added. Upon completion of addition 0.33 ml (0.0035 mole) of ethanesulfonyl chloride was added and the reaction mixture was stirred at 0° C. for one hour. After this time the reaction mixture was allowed to warm to ambient temperature where it stirred for 16 hours. Analysis of the reaction mixture by thin layer chromatography (TLC) indicated the presence of a small amount of starting material. An additional 0.05 ml of pyridine and 0.05 ml of ethanesulfonyl chloride were added and the reaction mixture was stirred at ambient temperature for one hour. Analysis of the reaction mixture by TLC indicated that the reaction had gone to completion. The reaction mixture was poured into water. The organic layer was separated and the water layer extracted with methylene chloride. The extracts and the organic layer were combined and washed in succession with aqueous 1N hydrochloric acid, aqueous saturated sodium bicarbonate solution, water, and aqueous saturated sodium chloride solution. The organic layer was dried with magnesium sulfate and filtered. The filtrate was concentrated under reduced pressure to a residue. The residue was dried under high vacuum to yield 1.45 g of 1-[4-chloro-2-fluoro-5-(N-ethylsulfonylamino)phenyl]-3-methyl-4-difluoro-methyl-$\Delta^2$-1,2,4-triazolin-5-one as an oily foam. The nmr spectrum was consistent with the proposed structure.

EXAMPLE 7

SYNTHESIS OF 1-[4-CHLORO-2-FLUORO-5-[(N-ETHYLSULFONYL-N-METHYL)AMINO]PHENYL]-3-METHYLL 2-1,2 4-TRIAZOLIN-5-ONE 4-DIFLUOROMETHYL-$\Delta^2$-1,2,4-TRIAZOLIN-5-ONE (COMPOUND 29)

To a stirred suspension of 0.095 g (0.0019 mole) of sodium hydride (50% in mineral oil) in dimethylformamide was added 0.7 g (0.0019 mole) of 1-[4-chloro-2-fluoro-5-(N-ethylsulfonylamino)phenyl]-3-methyl-4-difluoromethyl-$\Delta^2$-1,2,4-triazolin-5-one (prepared as in Examine 6). The reaction mixture was stirred until homogeneous, approximately 15 minutes. After this time 0.28 g (0.002 mole) of methyl iodide was added to the reaction mixture, which was then stirred for 16 hours. The reaction mixture was diluted with diethyl ether and washed with water. The organic layer was dried with sodium sulfate, filtered, and concentrated under reduced pressure to a residue. The residue was purified by column chromatography on silica gel using 50:1-methylene chloride:acetone as an eluent. The appropriate fractions were combined and concentrated under reduced pressure to yield 0.7 g of 1-[4-chloro-2-fluoro-5-[(N-ethylsulfonyl-N-methyl)amino]phenyl]-3-methyl-4-difluoromethyl-$\Delta^2$-1,2,4-triazolin-5-one; m.p. 101°-103.5° C.

The nmr spectrum was consistent with the proposed structure.

Analysis calc'd for $C_{13}H_{14}ClF_3N_4SO_5$: C39.15; H 3.54; N 14.05;

Found: C 39.46; H 3.57; N 13.91.

EXAMPLE 8

SYNTHESIS OF 1-(5-AMINO-4-BROMO-2-FLUORO-PHENYL)-3-METHYL-4-DIFLUOROMETHYL-$\Delta^2$-1,2,4-TRIAZOLIN-5-ONE AS AN INTERMEDIATE

Step

A Synthesis of Pyruvic Acid, 4-Bromo-2-fluoro-phenylhydrazone as an Intermediate This compound was prepared in a manner analogous to that of Example 1, Step D, using 24.3 g (0.128 mole) of commercially available 4-bromo-2-fluoroaniline, 11.3 g (0.128 mole) of pyruvic acid, 8.8 g (0.128 mole) of sodium nitrite and 63.2 g (0.28 mole) of stannous chloride in 48 ml of water and 214 ml of concentrated hydrochloric acid. The yield of pyruvic acid, 4-bromo-2-fluorophenylhydrazone was 27.2 g; m.p. 172°-173° C. The reaction was repeated several times.

Step B

Synthesis of 1-(4-Bromo-2-fluorophenyl)-3-methyl-$\Delta^2$-1,2,4-triazolin-5-one as an

Intermediate

This compound was prepared in a manner analogous to that of Example 1, Step E. The reaction was run in three batches using a total of 34.3 g (0.125 mole) of pyruvic acid, 4-bromo-2-fluorophenylhydrazone, 35.0 g (0.127 mole) of diphenylphosphoryl azide, and 12.6 g (0.125 mole) of triethylamine in 300 ml of toluene. The reaction mixtures were combined for isolation of product. The yield of 1 4-bromo-2-fluorophenyl)-3-methyl-$\Delta^2$1,2,4-triazolin-5-one was 271.0 g, m.p. 201°-203° C.

The nmr spectrum was consistent with the proposed structure. The reaction was repeated several times.

Step C

Synthesis of 1-(4-bromo-2-fluorophenyl)-3-methyl-4-difluoromethyl-$\Delta^2$-1,2,4-triazolin 5-one as an Intermediate This compound was prepared in a manner analogous to that of Example 1, Step F using 13.0 g (0.048 mole) of 1-(4-bromo-2-fluorophenyl)-3-methyl-$\Delta^2$-1,2,4-triazolin-5-one, 8.0 g (0.143 mole) hydroxide, 1.6 g (0.005 mole) of tetrabutylammonium bromide, and chlorodifluoromethane in 200 ml of tetrahydrofuran. The yield of 1-(4-bromo-2-fluoro-phenyl)-3-methyl-4-difluoromethyl-$\Delta^2$-1,2,4-tria zolin-5-one was 6.5 g. The reaction was repeated several times.

Step D

Synthesis of 1-(4-Bromo-2-fluoro-5-nitro-phenyl)-3-methyl-4-difluoromethyl-$\Delta^2$-1,2,4-triazolin-5-one as an

Intermediate

This compound was prepared in a manner analogous to that of Example 1, Step G using 7.0 g (0.022 mole) of 1-(4-bromo-2-fluorophenyl)-3-methyl-4-difluoro-methyl-$\Delta^2$-1,2,4-triazolin-5-one and 1. nitric acid in 9 ml of concentrated sulfuric acid. The yield of 1-(4-bromo-2-fluoro-5-nitrophenyl-3-methyl-4-difluoromethyl-$\Delta^2$-1,2,4-triazolin was 2.9 g; m.p. 99-105° C. The reaction was repeated several times.

Step E

Synthesis Of 1-(5-amino-4-bromo-2-fluoro-phenyl)-3-methyl-4-difluoromethyl-$\Delta^2$-1,2,4-triazolin-5-one as an

Intermediate

This compound was prepared in a manner analogous to that of Example 1, Step H using 2.5 g (0.007 mole) of 1-(4-bromo-2-fluoro-5-nitrophenyl)-3-methyl-4-difluoromethyl-$\Delta^2$-1,2,4-triazolin-5(0.027 mole) of powdered iron in 1 ml of water and 30 ml of acetic acid. The yield of 1-(5-amino-4[]bromo-2-fluorophenyl)-3-methyl-4-difluoromethyl-$\Delta^2$1,2,4-triazolin-5-one was 1.7 g; m.p. 117°-119° C.

The nmr spectrum was consistent with the proposed structure.

The reaction was repeated several times.

EXAMPLE 9

SYNTHESIS OF 1-[4-BROMO-2-FLUORO-5-[BIS(N-ETHYLSULFONYL)AMINO]PHENYL]-3-METHYL-4-DIFLUOROMETHYL-$\Delta^2$-1,2,4-TRIAZOLIN-5-ONE (COMPOUND 40)

This compound was prepared in a manner analogous to that of Example 2 using 1.6 g (0.0047 mole) of -(5-amino-4-bromo-2-fluorophenyl)-3-methyl-4-difluoromethyl-$\Delta^2$-1,2,4-triazolin-5-one (prep Example 8), 1.2 g (0.0095 mole) of ethanesulfonyl chloride, and 1.0 g (0.01 mole) of triethylamine in ml of methylene chloride. The yield of 1-[4-bromo-fluoro-5-[bis(N-ethylsulfonyl amino]phenyl]-3-methyl-difluoromethyl-$\Delta^2$-1,2,4-triazolin-5-one was 0.9 g; m.p. 145°-146° C.

The nmr spectrum was consistent with the proposed structure.

Analysis calc'd for $C_{14}H_{16}BrF_3N_4O_5S_2$: C32.25; H 3.09; N10.75;

Found: C 31.94; H 3.10; N 10.78.

EXAMPLE 10

SYNTHESIS OF 1-[4-BROMO-2-FLUORO-5-(N-ETHYLSULFONYLAMINO)PHENYL]-3-METHYL-4 DIFLUOROMETHYL-$\Delta^2$-1,2,4-TRIAZOLIN-5-ONE (COMPOUND 13)

This compound was prepared in a manner analogous to that of Example 2 using 0.52 g (0.001 mole) of -[4-bromo-2-fluoro-5-[bis(N-ethylsulfonyl)amino]-phenyl]-3-methyl-4-difluoromethyl-$\Delta^2$-1,2,4zolin-5-one (Prepared as in Example 9), and 0.1 g (0.0025 mole) of sodium hydroxide in 3 ml of water and 0 ml of methanol. The yield of 1-[4-bromo-2-fluoro-(N-ethylsulfonylamino)phenyl]-3-methyl-4-difluoro-methyl-$\Delta^2$-1,2,4-triazolin-5-one was 0.38 g; m.p. 140°141° C.

The nmr spectrum was consistent with the proposed structure.

EXAMPLE 11

SYSTHESIS OF 1-(5-AMINO-4-BROMO-2-FLUORO-PHENYL)-3,4-DIMETHYL-$\Delta^2$-1,2,4-TRIAZOLIN-5-ONE AS AN INTERMEDIATE

Step A

Synthesis of 1-(4-bromo-2-fluorophenyl)-3,4-dimethyl-$\Delta^2$-1,2,4-triazolin-5-one as an Intermediate This compound was prepared in a manner analogous to that of Example 7, using 6.0 g (0.022 mole) of 1-(4-bromo-2-fluorophenyl)-3-methyl-$\Delta^2$-1,2,4-tria-zolin-5-one (prepared as in Example 8, St 0.029 mole) of methyl iodide, and 1.1 g (0.022 mole) of 50% sodium hydride in 50 ml of dimethylformamide. The yield of 1-(4-bromo-2-fluorophenyl)-3,4-dimethyl$\Delta^2$-1 2,4-triazolin-5-one was 3.9 g; m.p. 122°-123.5° C.

The nmr spectrum was consistent with the proposed structure.

Step B

Synthesis of 1-(4-Bromo-2-fluoro-5-nitro-phenyl)-3,4-dimethyl-$\Delta^2$-1,2,4-triazolin-5-one as an Intermediate This compound was prepared in a manner analogous to that of Example 1, Step G using 3.7 g (0.013 mole) of 1-(4-bromo-2-fluorophenyl)-3,4-dimethyl-$\Delta^2$-1,2,4-triazolin-5-one and 0.98 g (0.016 acid in 15 ml of concentrated sulfuric acid. The yield of 1-(4-bromo-2-fluoro-5-nitrophenyl)-3,4-di-methyl-$\Delta^2$-1,2,4-triazolin-5-one was 2 151.5°-154.5° C.

The nmr spectrum was consistent with the proposed structure.

Step C

Synthesis of 1-(5-amino-4-bromo-2-fluoro-phenyl)-3,4-dimethyl-$\Delta^2$-1,2,4-triazolin-5-One as an Intermediate This compound was prepared in a manner analogous to that of Example 1, Step H using 2.3 g 0.007 mole) of 1-(4-bromo-2-fluoro-5-nitrophenyl)-3,4-dimethyl-$\Delta^2$-1,2,4-triazolin-5-one and 2.3 g in 1S ml of water and 35 ml of acetic acid. The yield of 1-(5-amino-4-bromo-2-fluorophenyl)-3,4-dimethyl-$\Delta^2$-1,2,4-triazolin-5-one was 1.2 g The nmr spectrum was consistent with the proposed structure.

EXAMPLE 12

SYNTHESIS OF 1-[4-BROMO-2-FLUORO-5-[BIS(N-ETHYLSULFONYL)AMINO]PHENYL]-3,4-DIMETHYL $\Delta^2$-1,2,4-TRIAZOLIN-5-ONE (COMPOUND 39)

This compound was prepared in a manner analogous to that of Example 2, using 0.95 g (0.008 mole) of 1-(5-amino-4-bromo-2-fluorophenyl)-3,4-dimethyl-$\Delta^2$-1,2,4-triazolin-5-one (prepared as in Ex 11) 1.0 g (0.008 mole) of ethanesulfonyl chloride, 11), 1. and 0.87 g of triethylamine in 25 ml of methylene chloride. The yield of 1-[4-bromo-2-fluoro-5-[bis-(N-ethylsulfonyl)amino]-phenyl]-3,4-dimethyl-$\Delta^2$1,2,4-triazolin-5-one was 1.4 g; m.p. 173°-174.5° C.

The nmr spectrum was consistent with the proposed structure.

Analysis calc'd for $C_{14}H_{18}BrFN_4O_5S_2$: C 36.64; H 3.74; N 11.54;

Found: C 33.72; H 3.57; N 10.64.

EXAMPLE 13

SYNTHESIS OF 1-(5-AMINO-2,4-DICHLOROPHENYL)-3-METHYL-4-DIFLUOROMETHYL-$\Delta^2$-1,2,4-TRIAZOLIN-5 ONE AS AN INTERMEDIATE

Step A

Synthesis of Pyruvic Acid, 2,4-Dichloro-phenylhydrazone as an Intermediate

To a stirred solution of 16.2 g (0.07 mole) of commercially available 2,4-dichlorophenylhydrazine hydrochloride in 100 ml of ethanol was added in one Portion 9.2 g (0.11 mole) of pyruvic acid in 100 ml of water. The reaction mixture was stirred for 10 minutes and the resultant solid collected by filtration to yield when dried 13.5 g of pyruvic acid, 2,4-dichlorophenylhydrazone, m.p. 193°-194° C. The reaction was repeated several times.

Step B

Synthesis of
1-(2,4-Dichlorophenyl)-3-methyl-$\Delta^2$-1,2,4-triazolin-5-one as an Intermediate This compound was prepared in a manner analogous to that of Example 1, Step E using 13.6 g (0.054 mole) of pyruvic acid, 2,4-dichlorophenylhydrazone, 14.9 g (0.054 mole) of diphenylphosphoryl azide, and 5.5 g (0.054 mole) of triethylamine in 100 ml of toluene. The yield of 1-(2,4-dichlorophenyl)-3-methyl-$\Delta^2$1,2,4-triazolin-5-one was 13.0 g; m.p. 174-175° C. The reaction was repeated several times.

Step C

Synthesis of
1-(2,4-Dichlorophenyl)-3-methyl-4-difluoromethyl-$\Delta^2$-1,2,4-triazolin-5-one as an Intermediate This compound was prepared in a manner analogous to that of Example 1, Step F using 16.0 g (0.065 mole) of 1-(2,4-dichlorophenyl)-3-methyl-$\Delta^2$-1,2,4-tria-zolin-5-one, chlorodifluoromethane, 7.3 g (0.13 mole) of potassium hydroxide and 10.5 g (0.03 mole) of tetrabutylammonium bromide in 150 ml of tetrahydrofuran. The yield of 1-(2,4-dichlorophenyl)-3-methyl-4-difluoromethyl-$\Delta^2$-1,2,4-triazolin-5-one was 4.1 g; times.

Step D

Synthesis of 1-(2,4-Dichloro-5-nitrophenyl)
3-methyl-4-difluoromethyl-$\Delta^2$-1,2,4-triazolin-5-one as an Intermediate This compound was prepared in the manner of Example 1, Step G using 4.0 g (0.013 mole) of 1-(2,4-dichlorophenyl)-3-methyl-4-difluoromethyl-$\Delta$triazolin-5-one and 1.2 ml (0.015 mole) of 70% nitric acid in 20 ml of concentrated sulfuric acid. The yield of 1-(2,4-dichloro-5-nitrophenyl)-3-methyl-4-di fluoromethyl-$\Delta^2$-1,2,4-triazolin-5-one was 3.0 g; m.p. 95°-97° C. The reaction was repeated several times.

Step E

Synthesis of
1-(5-Amino-2,4-dichlorophenyl)-3-methyl-4-difluoromethyl-$\Delta^2$-1,2,4-triazolin-5-one as an Intermediate This compound was prepared in a manner analogous to that of Example 1, Step H using 2.5 g (0.007 mole) of 1-(2,4-dichloro-5-nitrophenyl)-3-methyl-4-difluoromethyl-$\Delta^2$-1,2,4-triazolin-5-one and mole) of powdered iron in 6 ml of water and 60 ml of water. The yield of 1-(5-amino-2,4-dichlorophenyl)3-methyl-4-difluoromethyl-$\Delta^2$-1,2,4-triazolin-5-one was 2.0 g; m.p. 133°-135° C. The reaction was repeated several times.

EXAMPLE 14

SYNTHESIS OF
1-[2,4-DICHLORO-5-[BIS-(N-METHYLSULFONYL)AMINO]PHENYL]-3-METHYL-4-DIFLUOROMETHYL
$\Delta^2$-1,2,4-TRIAZOLIN-5-ONE (COMPOUND 22)

This compound was prepared in a manner analogous to that of Example 2 using 1.2 g (0.004 mole) of -(5-amino-2,4-dichlorophenyl)-3-methyl-4-difluoro-methyl-$\Delta^2$-1,2,4-triazolin-5-one (prepared as in Example 13), 0.97 g (0.009 mole) of methanesulfonyl chloride, and 0.95 g (0.009 mole) of triethylamine in 5 ml of methylene chloride. The yield of 1-[2,4-di-chloro-5-[bis(N-methylsulfonyl)amino]phenyl]-3-methyl-4-difluoromethyl-$\Delta^2$-1,2,4-triazolin-5-one was 1.3 m.p. 213°-214° C.

The nmr spectrum was consistent with the proposed structure.

Analysis calc'd for $C_{12}H_{12}Cl_2F_2N_4O_5S_2$: C 30.91; H 2.59; N 12.02;
Found: C 31.15; H 2.43; N 12.03.

EXAMPLE 15

SYNTHESIS OF
1-[2,4-DICHLORO-5-(N-METHYL-SULFONYLAMINO)PHENYL]-3-METHYL-4-DIFLUORO

METHYL-$\Delta^2$-1,2,4-TRIAZOLIN-5-ONE (COMPOUND 1)

This compound was prepared in a manner analogous to that of Example 3 using 0.8 g (0.002 mole) of 1-[2,4-dichloro-5-[bis(N-methylsulfonyl)amino]phenyl]-3- /) methyl-4-difluoromethyl-$\Delta^2$-1,2,4-triazolin-5-one (prepared as in Example 14) and 0.14 g (0.003 mole) of sodium hydroxide in 0.3 ml of water and 10 ml of ethanol. The yield of 1-[2,4-dichloro-5-(N-methylsul onylamino)phenyl]-3-methyl-4-difluoromethyl-$\Delta^2$-1,2,4-triazolin-5-one was 0.5 g; m.p. 75°-78° C.

The nmr spectrum was consistent with the proposed structure.

Analysis calc'd for $C_{11}H_{10}Cl_2F_2N_4O_3S$: C 34.21; H2.59; N14.51;
Found: C 33.98; H 2.62; N 14.20.

EXAMPLE 16

SYNTHESIS OF
1-(5-AMINO-2,4-DICHLOROPHENYL)-3-METHYL-$\Delta^2$-1,2,4-TRIAZOLIN-5-ONE AS AN INTERMEDIATE

Step A

Synthesis of 1-
2,4-Dichloro-5-nitrophenyl)-3-methyl-$\Delta^2$-1,2,4-triazolin-5-one as an Intermediate This compound was prepared in a manner analogous to that of Example 1, Step G using 6.0 g (0.025 mole) of 1-(2,4-dichlorophenyl)-3-methyl-$\Delta^2$-1,2,4-tria-zolin-5-one (prepared as an Example 13. Step B) 1.9 ml (0.03 mole) of 70% nitric acid in 25 ml of concentrated sulfuric acid. The yield of 1-(2,4-di-chloro-5-nitrophenyl)-3-methyl-$\Delta^2$-1,2,4-triazolin-one was 5.6 g as a solid.

Step B

Synthesis of
1-(5-Amino-2,4-dichlorophenyl)-3-methyl-$\Delta^2$-1,2,4-triazolin-5-one as an Intermediate To a 500 ml Parr hydrogenation bottle was added 0.5 g of platinum oxide, 100 ml of ethanol, then 6.4 g (0.022 mole) of 1-(2,4-dichloro-5-nitrophenyl)-3methyl $\Delta^2$-1,2,4-triazolin-5-one. The bottle was placed in a Parr hydrogenator and the reaction mixture shaken until the theoretical amount of hydrogen was taken up. The bottle was removed from the hydrogenator and the reaction mixture filtered. The filtrate was dried with sodium sulfate and refiltered. The filtrate was concentrated under reduced pressure to yield 4.5 g of 1-(5-amino-2,4-dichlorophenyl)-3methyl-$\Delta^2$-1,2,4-triazolin-5-one.

The nmr spectrum was consistent with the proposed

EXAMPLE 17

SYNTHESIS OF 1-[2,4-DICHLORO-5-[BIS(N-ETHYLSULFONYL)AMINO]PHENYL]-3-METHYL-4-ETHYL SULFONYL-$\Delta^2$-1,2,4-TRIAZOLIN-5-ONE (COMPOUND 36)

This compound was prepared in a manner analogous to that of Example 2, using 0.5 g (0.002 mole) of 1-(5-amino-2,4-dichlorophenyl)-3-methyl-$\Delta^2$-1,2,4-triazolin-5-one (prepared as in Example 16(0.006 mole) of ethanesulfonyl chloride and 0.7 g (0.007 mole) of triethylamine in 15 ml of methylene chloride. The yield of 1-[2,4-dichloro-5-[bis(Nethylsulfonyl)amino]phenyl]-3-methyl-4-ethylsulfonyl-$\Delta^2$-1,2,4-triazolin-5-one was 0.5 g; m.p. 215°-216° C.

The nmr spectrum was consistent with the proposed structure. The reaction was repeated several times.

Analysis calc'd for $C_{15}H_{20}Cl_2N_4O_7S_3$: C 33.64; H 3.77; N 10.46;

Found: C 33.88; H 3.91; N 10.68.

EXAMPLE 18

SYNTHESIS OF 1-[2,4-DICHLORO-5-(N-ETHYL-SULFONYLAMINO)PHENYL]-3-METHYL-$\Delta^2$-1,2,4-TRIAZOLIN-5-ONE This compound was prepared in a manner analogous to that of Example 3, using 0.9 g(0.002 mole) of 1-[2,4-dichloro-5-[bis(N-ethylsulfonyl)amino]phenyl]--ethylsulfonyl-$\Delta^2$-1,2,4-triazolin-5-one (prepared as in Example 17) and 0.2 g(0.005 mole) sodium hydroxide in 0.25 ml of water and 12 ml of ethanol. The yield of 1-[2,4-dichloro-5-(N-ethylsulfonylamino)phenyl]-3-methyl $\Delta^2$-1,2,4-triazolin-5-one was 0.5 g; m.p. 221-222.5° C.

The nmr spectrum was consistent with the proposed structure.

Analysis calc'd for $C_{10}H_{10}Cl_2F_2N_4O_3S$: C 34.21; H2.58; N14.51;

Found: C 33 98; H 2.62; N 14.20.

EXAMPLE 19

SYNTHESIS OF 1-[4-CHLORO-2-FLUORO-5-(N-ETHYLSULFONYLAMINO)PHENYL]-3-METHYL-4-DIFLUOROMETHYL-$\Delta^2$-1,2,4-TRIAZOLIN-5-ONE (COMPOUND 11)

A stirred suspension of 1.0 g 34 mole) of 1-(4-amino-4-chloro-2-fluorophenyl)-3-methyl-4-difluoro-methyl-$\Delta^2$-1,2,4-triazolin-5-one in 5 ml of methyl chloride was cooled in an ice water bath and 0.3 ml (0.0037 mole) of pyridine was added. Upon completion of additional 0.33 ml (0.0035 mole) of ethanesulfonyl chloride was added and the reaction mixture was stirred at 0° C. for one hour. After this time the reaction mixture was allowed to warm to ambient temperature where it stirred for 16 hours. Analysis of the reaction mixture by thin layer chromatography (TLC) indicated the presence of a small amount of starting material. An additional 0.05 ml of pyridine and 0.05 ml of ethanesulfonyl chloride were added and the reaction mixture was stirred at ambient temperature for one hour. Analysis of the reaction mixture by TLC indicated that the reaction had gone to completion. The reaction mixture was poured into water. The organic layer was separated and the water layer extracted with methylene chloride. The extracts and the organic layer were combined and washed in succession with aqueous 1N hydrochloric acid, aqueous saturated sodium bicarbonate solution, water, and aqueous saturated sodium chloride solution. The organic layer was dried with magnesium sulfate and filtered. The filtrate was concentrated under reduced pressure to a residue. The residue was dried under high vacuum to yield 1.45 g of 1-[4-chloro-2-fluoro-5-(N-ethylsulfonylamino)phenyl]-3-methyl-4-methyl-A2-1,2,4-triazolin-5-one as an oily foam. The nmr spectrum was consistent with the proposed structure.

EXAMPLE 20

4-CHLORO-2-FLUORO-5-(N-ETHYLSULFONYLAMINO)ANILINE

Step A

2-Fluoro-5-Nitroacetanilide

To a stirred solution of 18.0 g (0.11 mole) of 2-fluoro-5-nitroaniline in 100 ml of dioxane was added 15.3 g (0.15 mole) of acetic anhydride. The reaction mixture was heated at reflux for two hours. The solvent was removed from the mixture by distillation under reduced pressure leaving a solid residue. This residue was stirred in 25 ml of methylene chloride and filtered. The filter cake was dried to yield 20.5 g of 2-fluoro-5nitroacetanilide, m.p. 177°-178° C.

Step B

5-Amino-2-fluoroacetanilide

Hydrogenation of 20.20 g (0.10 mole) of 2-fluoro-5nitroacetanilide with a catalytic amount (0.3 g) of platinum oxide in 200 ml of an ethanol/ethylacetate (80/20) solution yielded 16.0 g of 5-amino-2-fluoroacetanilide as a solid.

Step C

2-Fluoro-bis(N-ethylsulfonylamino) acetanilide

To a stirred mixture of 15.4 g (0.091 mole) of 5-amino-2-fluoroacetanilide in 75 ml of methylene chloride was added 18.5 g 0.183 mole) of triethyl amine. To this mixture was added slowly 23.5 g (0.183 mole) of ethyl sulfonyl chloride. The resultant mixture was stirred at room temperature for approximately 18 hours. The reaction mixture was passed through a column of silica gel, eluting with methylene chloride, to yield 12.0 g of 2-fluoro-5-bis(N-ethylsulfonylamino)acetanilide.

Steps A-C were repeated to prepare additional 2-fluoro-5-bis(N-ethylsulfonylamino)acetanilide.

Step D

2-Fluoro-5-(N-ethylsulfonylamino)-acetanilide

To a stirred solution of 27.0 g 0.007 mole) of 2-fluoro-5-bis(N-ethylsulfonylamino)acetanilide in 100 ml of dioxane was added a solution of sodium hydroxide (5.65 g, (0.0141 mole)) in 20 ml of water. Approximately 100 ml of water was added and the resultant solution was stirred at room temperature for about 15 minutes. The dioxane solvent was removed from the solution by extraction with diethyl ether. The remaining aqueous phase was acidified with concentrated hydrochloric acid forming a precipitate. The precipitate was collected by filtration and dried to yield 14.8 g of 2-fluoro-5-(N-ethylsulfonylamino)acetanilide, m.p. 175.5°- 177°

C. Additional product (1.9 g) was collected by extracting the filtrate with ethyl acetate and evaporating the extract after drying over anhydrous magnesium sulfate.

The nmr and ir spectra were consistent with the proposed structure.

Step E

4-Chloro-2-fluoro-5-(N-ethylsulfonylamino)-acetanilide

To a stirred solution of 8.0 g (0.031 mole) of 2-fluoro-5-(N-ethylsulfonylamino)acetanilide in 200 ml of dioxane was added slowly 2.5 ml (0.031 mole) of thionyl chloride. This mixture was heated at 80° C. for two days. The mixture was poured into ice water and the mixture was extracted with ethyl acetate. The extract was dried over anhydrous magnesium sulfate and filtered. The filtrate was evaporated under reduced pressure to yield 8.1 g of 4-chloro-2-fluoro-5-(N-ethylsulfonylamino)acetanilide.

Step F

4-Chloro-2-fluoro-5-(N-ethylsulfonylamino)-aniline

A stirred mixture of 2.0 g (0.0068 mole) of 4-chloro-2-fluoro-5-(N-ethylsulfonylamino)acetanilide and 0.84 g (0.020 mole) of sodium hydroxide in 100 ml of water was heated at reflux for approximately 18 hours. The reaction mixture was cooled and neutralized with concentrated hydrochloric acid. The neutralized mixture was extracted with ethylacetate. The extract was washed with an aqueous, saturated sodium chloride solution. The washed extract was dried over anhydrous magnesium sulfated and filtered. The filtrate was evaporated under reduced pressure to yield 2.7 g of 4-chloro-2-fluro -5-(N-ethylsulfonylamino)aniline as a solid.

The nmr was consistent with the proposed structure.

Step E

4-Chloro-2-fluoro-5-(N-ethylsulfonylamino)-acetanilide

To a stirred solution of 8.0 g (0.031 mole) of 2-fluoro-5-(N-ethylsulfonylamino)acetanilide in 200 ml of dioxane was added slowly 2.5 ml (0.03 mole) of thionyl chloride. This mixture was heated at 80° C. for two days. The mixture was poured into ice water and the mixture was extracted with ethyl acetate. The extract was dried over anhydrous magnesium sulfate and filtered. The filtrate was evaporated under reduced pressure to yield 8.1 g of 4-chloro-2-fluoro-5-(N-ethylsulfonylamino)acetanilide.

Step F

4-Chloro-2-fluoro-5-(N-ethylsulfonylamino)-aniline

A stirred mixture of 2.0 g (0.0068 mole) of 4-chloro-2-fluoro-5-(N-ethylsulfonylamino)acetanilide and 0.84 g (0.020 mole) of sodium hydroxide in 100 ml of water was heated at reflux for approximately 18 hours. The reaction mixture was cooled and neutralized with concentrated hydrochloric acid. The neutralized mixture was extracted with ethylacetate. The extract was washed with an aqueous, saturated sodium chloride solution. The washed extract was dried over anhydrous magnesium sulfate and filtered. The filtrate was evaporated under reduced pressure to yield 2.7 g of 4-chloro-2-fluoro-5-(N-ethylsulfonylamino)aniline as a solid.

The nmr was consistent with the proposed structure.

RICE BLAST TESTING PROCEDURE

Preparation of Inoculum

Media Preparation: A mixture of 5.0 g of agar in 500 mL of water was heated until the agar melted. A mixture of 40.0 g of Quaker Instant Oatmeal in 250 mL of water was added. The mixture was placed in an autoclave and was heated at 121° C. for 0.5 hour. After cooling, approximately 50 mL of the media was poured into each of 15 petri dishes.

Inoculum Preparation: Under sterile conditions, each petri dish was inoculated with mycelial plugs of *Pyricularia oryzae* (race IB-49) onto the surface of the media. The inoculated plates were incubaed for seven to ten days in a growth chamber at 25° c. approximately 40% humidity, and a photo period of 12 hours of light and 12 hours of dark using fluorescent lamps. The mycelia from the incubated plates were scraped into a beaker, and the resulting mixture was blended. This mixture was filtered through cheesecloth, and the filtrate which contained the rice blast spores was saved for the inoculation of rice plants.

Rice Treatment

Plastic pots (7 cm ×7 cm ×6.5 cm) were filled to an approximate depth of 4.5 cm with steam-sterilized sandy loam soil. The soil was leveled and pressed with a flat templet. Approximately 10 to 15 seeds of rice were placed on the flattened soil, and the seeds were firmly pressed into soil. A topping soil of equal proportions of sand and sandy loam soil was placed uniformly on top of each flat to a depth of approximately 0.5 cm.

The pots were placed in a greenhouse and watered regularly for 14 days after which the pots were drenched with a solution of the test compounds as described below. One day post treatment the rice plants were inoculated with the rice blast spore suspension using a DeVilbiss hand held sprayer. The inoculated plants were immediately place din a dark, humidified growth chamber (72° F., 88% humidity) for 24 hours. The flats were moved to a greenhouse and were bottom watered for the duration of the test.

The test compounds were applied as 50 g/liter flowable or an emulsifiable concentrate at rates equivalent to 0.125 kg/ha or submultiples thereof, i.e., 0.313 kg/ha, 0.0078 kg/ha, and so on. The applications were made as soil drenches using 20 mL of test solution of the appropriate concentration for each of three pots per compound.

For pots the size described above, an application rate of 0.125 kg/ha of test compound is equivalent to 0.000079 g/pot. A solution of 0.000435 g of test compound in 120 mL of distilled water containing 0.5% v/v of sorbitan monolaurate emulsifier/solubilizer was prepared. For application as a soil drench to the test pots, 60 mL of this solution was divided equally between the three pots (i.e. 20 mL per pto). The remaining 60 mL of the 0.125 kg/ha solution was decanted into 60 mL of the distilled water/emulsifier solution to produce a 120 mL solution containing 0.000217 g of the test compound, a rate of 0.0625 kg/ha. Sixty mL of this solution was decanted into 60 mL of the water/emulsifier solution to produce 120 mL of a mixture which contained 0.000108 g of the test compound, a rate of 0.0313 kg/ha. The process above was repeated, i.e., 60 mL of the 0.0313 kg/ha solution was used for the soil drench application and 60 mL was decanted into 60 mL of water/emulsifier solution for the 0.0156 kg/ha rate, etc.

The rice plant injury (phyotoxicity) and fungicidal activity were recorded at seven days post treatment. Phytotoxicity data were taken as percent control.

HERBICIDAL ACTIVITY

The plant test species used in demonstrating the herbicidal activity of compounds of this invention include cotton (*Gossvoium hirsutum* var. Stoneville), soybean (*Glvcine max* var. Williams), field corn (*Zea . mays* var. Agway 5955), rice (*Orvza sativa* var. Labelle), wheat (*Triticum aestivium* var. Prodax), field bindweed (*Convolvulus arvensis*), morningglory (*Ioomea lacumosa* or *Ioomea hederacea*), velvetleaf (*Abutilon theoohrasti*), barnyardgrass (*Echinochloa crus-oalli*), green foxtail (*Setaria viridis*), and johnsongrass (*Sorohum haleoense*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a 50/50 mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8-10 days, then the foliage of the emerged test plants was sprayed with a solution of the test compound in acetone-water containing up to 0.5% sorbitan monolaurate. After spraying the foliage was kept dry for 24 hours, then watered regularly for 21 days, and phytotoxicity data recorded.

Phytotoxicity data were taken as percent control. Percent control was determined by a method similar to the 0 to 100 rating system disclosed in "Research Methods In Weed Science," 2nd ed., B. Truelove, Ed.: Southern Weed Science Society; Auburn University, Auburn, Ala., 1977. The present rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe effect | Crop nearly destroyed, a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in Tables 3 and 4 below. The test compounds are identified in the tables by numbers which correspond to those in Table 1.

In the tables of herbicidal data below:

"kg/ha" is kilograms per hectare, and

"% C" is percent control.

It is clear that the generic class of aryltriazolinones described and illustrated herein is characterized by herbicidal activity, and that the degree of this activity varies among specific compounds within this class and to some extent among the species of plant to which these compounds may be applied. Thus, selection of a specific herbicidal compound for control of a specific plant may readily be made.

For herbicidal application, the active compounds as above defined are formulated into herbicidal compositions, by admixture, in herbicidally effective amounts, with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as watersoluble or water-dispersible granules, as powdery dusts, as wettable powders, as emulsifiable concentrates, as solutions, or as any of several other known types of formulations, depending no the desired mode of application.

For preemergence application these herbicidal compositions are usually applied either as sprays, dusts, or granules in the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing, or emulsifying agents used in agricultural formulations include, for example, the alkyl and alkylaryl sulfonates and sulfates and their sodium salts, polyhydric alcohols, and other types of surface active agents, many of which are available in commerce. The surface active agent, when used, normally comprises 1% to 15% by weight of the herbicidal composition.

For instance an emulsifiable concentrate may have the following composition (in % by weight):

| | |
|---|---|
| Active ingredient A | 40.00 |
| Antimicrobial agent | 0.5 |
| Foam suppressant | 0.10 |
| Surfactant C | 2.60 |
| Surfactant D | 0.40 |
| Thickener | 0.35 |
| Suspending agent | 0.45 |
| Propylene glycol (antifreeze) | 6.00 |
| Water | 50.05 |
| Total | 100.00 |

The antimicrobial agent is sodium o-phenylphenate tetrahydrate sold under the trademark and designation "Dowacide A". The foam suppressant is a water dilutable silicone emulsion sold under the trademark and designation "Dow Corning AF". Surfactant C is a nonionic paste of a condensate of ethylene oxide with a hydrophobic base formed by condensing propylene oxide with propylene glycol, sold under the trademark and designation "Pluronic P-84."Surfactant D is an anionic liquid comprising the sodium salt of a complex organic phosphate ester, sold under the trademark and designation "GAFAC LO-529."The thickener is a xanthan gum sold under the trademark and designation "Kelzan-M". The suspending agent is a colloidal magnesium aluminum silicate sold under the trademark and designation "Veegum." In use, by the farmer, this concentrate may be diluted with water to provide an aqueous composition containing, say about ¼% to 1½% of the active ingredient, for use on the field.

Other useful formulations for herbicidal applications include simple solutions of the active ingredient in a solvent in which it is completely soluble at the desired concentration, such as acetone, alkylated naphthalenes, xylene, or other organic solvents. Thus a suitable solution may contain, for instance, some 65% of the active ingredient, together with a minor proportion (say 1 to 10%) of a surfactant; for use on the field, this solution may be diluted with water, by the farmer, to provide an aqueous composition containing, say about ¼% to 1 ½% of the active ingredient. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon ®fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds; these may be diluted with water, by the farmer, to provide an aqueous composition containing say about ¼to 1½% of the active ingredient, for use on the field.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as 50, 100, 200 or 300 g/ha.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)-acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6(ethylamino)-1,3,5-triazin-2-yl]amino-2-methylpropanenitril (cyanazine); dinitroaniline herbicides such as 2,6-dinitro-N,N-dipropyl-4-(trifluoromethyl)benzeneamine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and other heterocyclic nitrogen herbicides such as 2-(2-(chlorophenyl)methyl)-4,4-dimethyl-3-isoxazolidinone (clomazone). For instance, one may mix Compound 1 of Table 1 with another herbicide that gives greater control of grassy weeds, such as alachlor, metolachlor, trifluralin or clomazone; the proportions may be such as to provide 0.3 to 0.5 part of Compound 1 together with about 0.5 to 0.8 part of either trifluralin or clomazone, or together with about 1.5 to 2 parts of either alachlor or metolachlor, e.g. in formulations applied pre-emergently at such a rate as to provide about 0.3 to 0.5 pound per acre of said Compound 1, for such crops as soybeans, corn (particularly when the corn seeds have been safened by treatment with 1,8-naphthalic anhydride, applied to the seeds at a rate of, say 0.5% of the seed weight) and sugarcane.

It is apparent that various modifications may be made in the formulation and application of the compounds of this invention without departing from the inventive concepts herein as defined in the claims.

TABLE 1
Representative Compounds

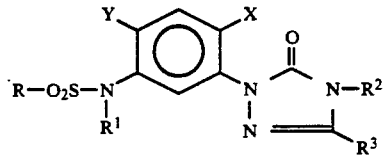

| Cpd | X | Y | R | $R^1$ | $R^2$ | $R^3$ |
|---|---|---|---|---|---|---|
| 1 | Cl | Cl | $CH_3$ | H | $CHF_2$ | $CH_3$ |
| 2 | F | F | $CH_3$ | H | $CHF_2$ | $CH_3$ |
| 3 | F | Cl | $CH_3$ | H | $CHF_2$ | $CH_3$ |
| 4 | F | Br | $CH_3$ | H | $CHF_2$ | $CH_3$ |
| 5 | F | $CH_3$ | $CH_3$ | H | $CHF_2$ | $CH_3$ |
| 6 | $CH_3$ | $CH_3$ | $CH_3$ | H | $CHF_2$ | $CH_3$ |
| 9 | Cl | Cl | $C_2H_5$ | H | $CHF_2$ | $CH_3$ |
| 10 | F | F | $C_2H_5$ | H | $CHF_2$ | $CH_3$ |
| 11 | F | Cl | $C_2H_5$ | H | $CHF_2$ | $CH_3$ |
| 12 | F | Br | $C_2H_5$ | H | $CHF_2$ | $CH_3$ |
| 13 | F | Br | $C_2H_5$ | H | $CHF_2$ | $CH_3$ |
| 14 | $CH_3$ | $CH_3$ | $C_2H_5$ | H | $CHF_2$ | $CH_3$ |
| 15 | F | Br | $C_2H_5$ | H | $(CH_2)_3F$ | $CH_3$ |
| 16 | Cl | Cl | $n$-$C_3H_7$ | H | $CHF_2$ | $CH_3$ |
| 17 | F | F | $n$-$C_3H_7$ | H | $CHF_2$ | $CH_3$ |
| 18 | F | Cl | $n$-$C_3H_7$ | H | $CHF_2$ | $CH_3$ |
| 19 | F | Br | $n$-$C_3H_7$ | H | $CHF_2$ | $CH_3$ |
| 20 | F | Cl | $CH_3$ | $C_2H_5$ | $CHF_2$ | $CH_3$ |
| 21 | F | Cl | $CH_3$ | $n$-$C_3H_7$ | $CHF_2$ | $CH_3$ |
| 22 | Cl | Cl | $CH_3$ | $SO_2CH_3$ | $CHF_2$ | $CH_3$ |
| 23 | F | F | $CH_3$ | $SO_2CH_3$ | $CHF_2$ | $CH_3$ |
| 24 | F | Cl | $CH_3$ | $SO_2CH_3$ | $CHF_2$ | $CH_3$ |
| 25 | F | Br | $CH_3$ | $SO_2CH_3$ | $CHF_2$ | $CH_3$ |
| 26 | F | $CH_3$ | $CH_3$ | $SO_2CH_3$ | $CHF_2$ | $CH_3$ |
| 27 | $CH_3$ | $CH_3$ | $CH_3$ | $SO_2CH_3$ | $CHF_2$ | $CH_3$ |
| 28 | F | Cl | $CH_3$ | $SO_2CH_5$ | $CHF_2$ | $CH_3$ |
| 29 | F | Cl | $C_2H_5$ | $CH_3$ | $CHF_2$ | $CH_3$ |
| 30 | F | Cl | $C_2H_5$ | $C_2H_5$ | $CHF_2$ | $CH_3$ |
| 31 | F | Cl | $C_2H_5$ | $n$-$C_3H_7$ | $CHF_2$ | $CH_3$ |
| 32 | F | Cl | $C_2H_5$ | $i$-$C_3H_7$ | $CHF_2$ | $CH_3$ |
| 33 | F | Cl | $C_2H_5$ | $CH_2OCH_3$ | $CHF_2$ | $CH_3$ |
| 35 | Cl | Cl | $C_2H_5$ | $SO_2C_2H_5$ | $CHF_2$ | $CH_3$ |
| 36 | Cl | Cl | $C_2H_5$ | $SO_2C_2H_5$ | $SO_2C_2H_5$ | $CH_3$ |
| 37 | F | F | $C_2H_5$ | $SO_2C_2H_5$ | $CHF_2$ | $CH_3$ |
| 38 | F | Cl | $C_2H_5$ | $SO_2C_2H_5$ | $CHF_2$ | $CH_3$ |
| 39 | F | Br | $C_2H_5$ | $SO_2C_2H_5$ | $CH_3$ | $CH_3$ |
| 40 | F | Br | $C_2H_5$ | $SO_2C_2H_5$ | $CHF_2$ | $CH_3$ |
| 41 | $CH_3$ | $CH_3$ | $C_2H_5$ | $SO_2C_2H_5$ | $CHF_2$ | $CH_3$ |
| 42 | F | Br | $C_2H_5$ | $SO_2C_2H_5$ | $(CH_2)_3F$ | $CH_3$ |
| 43 | Cl | Cl | $n$-$C_3H_7$ | $SO_2C_3H_7(n)$ | $CHF_2$ | $CH_3$ |
| 44 | F | F | $n$-$C_3H_7$ | $SO_2C_3H_7(n)$ | $CHF_2$ | $CH_3$ |
| 45 | F | Cl | $n$-$C_3H_7$ | $SO_2C_3H_7(n)$ | $CHF_2$ | $CH_3$ |
| 46 | F | Br | $n$-$C_3H_7$ | $SO_2C_3H_7(n)$ | $CHF_2$ | $CH_3$ |
| 47 | F | Cl | $CH_3$ | $CH_3$ | $CHF_2$ | $CH_3$ |
| 48 | F | Cl | $CH_3$ | H | $CHF_2$ | $CH_3$ |
| 49 | F | Cl | $CH_3$ | $n$-$C_4H_9$ | $CHF_2$ | $CH_3$ |
| 50 | Cl | Cl | $CH_3$ | $C_2H_5$ | $CHF_2$ | $CH_3$ |
| 51 | Cl | Cl | $CH_3$ | $n$-$C_3H_7$ | $CHF_2$ | $CH_3$ |
| 52 | Cl | Cl | $CH_3$ | $n$-$C_4H_9$ | $CHF_2$ | $CH_3$ |
| 53 | F | Cl | $C_6H_5$ | H | $CHF_2$ | $CH_3$ |
| 54 | F | Cl | $N(CH_3)_2$ | H | $CHF_2$ | $CH_3$ |
| 55 | F | Cl | $N(C_2H_5)_2$ | H | $CHF_2$ | $CH_3$ |
| 56 | F | Cl | OH | H | $CHF_2$ | $CH_3$ |
| 57 | F | Cl | $CH_3$ | $CHF_2$ | $CHF_2$ | $CH_3$ |
| 58 | Cl | F | $CH_3$ | $SO_2CH_3$ | $CHF_2$ | $CH_3$ |
| 59 | Cl | F | $C_2H_5$ | $SO_2C_2H_5$ | $CHF_2$ | $CH_3$ |
| 60 | Cl | F | $CH_3$ | H | $CHF_2$ | $CH_3$ |
| 61 | Cl | F | $C_2H_5$ | H | $CHF_2$ | $CH_3$ |
| 62 | $CH_3$ | Cl | $CH_3$ | $SO_2CH_3$ | $CHF_2$ | $CH_3$ |
| 63 | $CH_3$ | Cl | $CH_3$ | H | $CHF_2$ | $CH_3$ |
| 64 | F | $NO_2$ | $CH_3$ | $SO_2CH_3$ | $CHF_2$ | $CH_3$ |

TABLE 1-continued

Representative Compounds

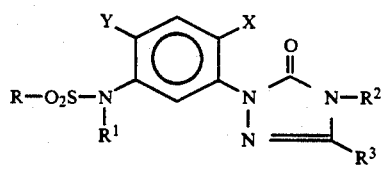

| Cpd | X | Y | R | R¹ | R² | R³ |
|---|---|---|---|---|---|---|
| 65 | F | NO₂ | CH₃ | H | CHF₂ | CH₃ |
| 66 | F | OCHF₂ | CH₃ | SO₂CH₃ | CHF₂ | CH₃ |
| 67 | F | OCHF₂ | CH₃ | H | CHF₂ | CH₃ |
| 68 | F | CF₃ | CH₃ | SO₂CH₃ | CHF₂ | CH₃ |
| 69 | F | CF₃ | CH₃ | H | CHF₂ | CH₃ |
| 70 | F | Cl | | —(CH₂)₃— | CHF₂ | CH₃ |
| 71 | F | Cl | | —(CH₂)₄— | CHF₂ | CH₃ |
| 72 | F | Cl | | —(CH₂)₅— | CHF₂ | CH₃ |
| 73 | F | Cl | | —(CH₂)₆— | CHF₂ | CH₃ |
| 74 | F | Cl | CH₂COOH | H | CHF₂ | CH₃ |
| 75 | F | Cl | CH₃ | OCH₃ | CHF₂ | CH₃ |
| 76 | F | Cl | CH₃ | CH₂CH₂CH₂F | CHF₂ | CH₃ |
| 77 | F | Cl | CH₃ | H | CHF₂ | OCH₃ |
| 78 | F | Cl | CH₃ | SO₂CH₃ | CHF₂ | OCH₃ |
| 79 | F | Cl | CH₃ | SO₂CH₃ | CHF₂ | Cl |
| 80 | F | Cl | CH₃ | H | CHF₂ | Cl |
| 81 | F | Cl | CH₃ | H | CHF₂ | H |
| 82 | F | Cl | CH₃ | H | CHF₂ | SO₂CH₃ |
| 83 | F | Cl | CH₃ | H | CHF₂ | SOCH₃ |
| 84 | F | Cl | CH₃ | H | CHF₂ | SCH₃ |
| 85 | F | Cl | C₆H₄(4-Cl) | H | CHF₂ | CH₃ |
| 86 | F | Cl | C₆H₄(4-CH₃) | H | CHF₂ | CH₃ |
| 87 | F | Cl | C₆H₄(4-OCH₃) | H | CHF₂ | CH₃ |
| 88 | Br | Cl | CH₃ | H | CHF₂ | CH₃ |
| 89 | Br | Br | CH₃ | H | CHF₂ | CH₃ |
| 90 | Br | CF₃ | CH₃ | H | CHF₂ | CH₃ |
| 91 | F | Cl | CH₃ | CH₂COOH | CHF₂ | CH₃ |
| 92 | F | Cl | C₂H₅ | CH₂COOH | CHF₂ | CH₃ |
| 93 | F | Cl | CH₃ | CH₂C₆H₅ | CHF₂ | CH₃ |
| 94 | F | Cl | CH₃ | CH₂C₆H₃(2,4-Cl₂) | CHF₂ | CH₃ |
| 95 | F | Cl | C₂H₅ | CH₂C₆H₅ | CHF₂ | CH₃ |
| 96 | F | Cl | CH₃ | CH₂CH=CH₂ | CHF₂ | CH₃ |
| 97 | F | Cl | C₂H₅ | CH₂C—CH | CHF₂ | CH₃ |
| 98 | F | Cl | C₂H₅ | OCH₃ | CHF₂ | CH₃ |
| 99 | Cl | Cl | CF₃ | H | CHF₂ | CH₃ |
| 100 | F | Cl | CHF₂ | H | CHF₂ | CH₃ |

Other representative compounds are those which are identical with compounds 20, 21, 29-33, 47-87, and 91 to 100 respectively, except that X is F and Y is Br. Still other representative compounds are those which are identical with compounds 1 to 87 and 91 to 100 respectively, except that X is F and Y is CF₃. Other representative compounds are those that are identical to compounds 9 to 87 and 91 to 100 respectively, except that X is Br. Other representative compounds are those which are identical with compounds 1-19, 48, 53-56, 60, 61, 63, 65, 67, 69, 71, 74, 77, 80-87 respectively, except that R¹ is Na (or other salt-forming group). Other representative compounds are those which are identical with compounds 1-100, respectively, except that R² is —CF₂CHF₂.

Compounds in which R¹ is H, such as Compound 1, used preemergently have shown a selectivity favorable to soybeans. Compounds in which R¹ is alkyl, such as Compound 31, used pre-emergently, have shown a selectivity favorable to cotton. Compound 1 pre-emergently applied also shows good corn tolerance. These are effective at low rates of application.

TABLE 2

Characterizing Data

| Cmpd No. | M.P. (°C) | Empirical Formula | | Elemental Analysis | | |
|---|---|---|---|---|---|---|
| | | | | C | H | N |
| 1 | 75-78(d)* | C₁₁H₁₀Cl₂F₂N₄O₃S | C | 34.21 | 2.59 | 14.51 |
| | | | F | 33.98 | 2.62 | 14.20 |
| 2 | 160-161 | C₁₁H₁₀F₄N₄O₃S | C | 37.29 | 2.85 | 15.81 |
| | | | F | 37.33 | 2.75 | 16.00 |
| 3 | 156-159 | C₁₁H₁₀ClF₃N₄O₃S | C | 34.79 | 2.65 | 14.75 |
| | | | F | 35.47 | 2.53 | 14.94 |
| 4 | 162-163 | C₁₁H₁₀BrF₃N₄O₃S | C | 31.82 | 2.43 | 13.49 |
| | | | F | 31.93 | 2.31 | 13.28 |
| 5 | 136-138 | C₁₃H₁₃F₃N₄O₃S | C | 41.14 | 3.74 | 15.99 |
| | | | F | 41.20 | 3.88 | 15.74 |
| 6 | 140-141 | C₁₃H₁₆F₂N₄O₃S | | | | |
| 9 | 126-128 | C₁₂H₁₂Cl₂F₂N₄O₃S | C | 35.92 | 3.02 | 13.96 |
| | | | F | 35.83 | 3.00 | 13.95 |
| 10 | 118-119 | C₁₂H₁₂F₄N₄O₃S | C | 39.13 | 3.28 | 15.21 |
| | | | F | 38.92 | 3.44 | 15.20 |
| 11 | 162-163 | C₁₂H₁₂ClF₃N₄O₃S | C | 37.46 | 3.14 | 14.56 |
| | | | F | 37.65 | 3.12 | 14.44 |
| 12 | 218.5-220 | C₁₂H₁₄BrFN₄O₃S | C | 36.65 | 3.59 | 14.25 |
| | | | F | 36.94 | 3.48 | 14.17 |
| 13 | 140-141 | C₁₂H₁₂BrF₃N₄O₃S | | | | |
| 14 | 123-124 | C₁₄H₁₈F₂N₄O₃S | | | | |
| 15 | 152-153 | C₁₄H₁₇BrF₂N₄O₃S | C | 38.28 | 3.90 | 12.75 |
| | | | F | 38.33 | 3.92 | 12.60 |
| 16 | 159-162 | C₁₂H₁₄Cl₂F₂N₄O₃S | C | 37.60 | 3.40 | 13.49 |
| | | | F | 37.60 | 3.15 | 13.53 |
| 17 | 107-108 | C₁₃H₁₄F₄N₄O₃S | C | 40.84 | 3.70 | 14.65 |

TABLE 2-continued

Characterizing Data

| Cmpd No. | M.P. (OC) | Empirical Formula | | C | Elemental Analysis H | N |
|---|---|---|---|---|---|---|
| 18 | 95–96 | $C_{13}H_{14}ClF_3N_4O_3S$ | F<br>C<br>F | 40.54<br>39.18<br>38.07 | 3.47<br>3.54<br>3.60 | 14.51<br>14.05<br>14.05 |
| 19 | 114–115 | $C_{13}H_{14}BrF_3N_4O_3S$ | | | | |
| 20 | 112–116 | $C_{13}H_{14}ClF_3N_4O_3S$ | | | | |
| 21 | 108–111 | $C_{14}H_{16}ClF_3N_4O_3S$ | | | | |
| 22 | 213–214 | $C_{12}H_{12}Cl_2F_2N_4O_5S_2$ | C<br>F | 30.91<br>31.15 | 2.59<br>2.43 | 12.02<br>12.03 |
| 23 | 175–180 | $C_{12}H_{12}F_4N_4O_5S_2$ | C<br>F | 33.33<br>33.25 | 2.80<br>2.85 | 12.96<br>12.93 |
| 24 | 180–196 | $C_{12}H_{12}ClF_3N_4O_5S_2$ | C<br>F | 32.11<br>31.98 | 2.69<br>2.32 | 12.98<br>12.15 |
| 25 | 192–194 | $C_{12}H_{12}F_3N_4O_5S_2$ | C<br>F | 29.22<br>29.19 | 2.45<br>2.42 | 11.36<br>11.32 |
| 26 | 172–176 | $C_{13}H_{15}F_3N_4O_5S_2$ | | | | |
| 27 | 208–209 | $C_{14}H_{18}F_2N_4O_5S_2$ | | | | |
| 28 | 128–131 | $C_{13}H_{14}ClF_3N_4O_5S_2$ | C<br>F | 33.73<br>33.57 | 3.05<br>3.17 | 12.11<br>12.12 |
| 29 | 104–104 | $C_{13}H_{14}ClF_3N_4O_3S$ | C<br>F | 39.15<br>39.46 | 3.54<br>3.57 | 14.05<br>13.91 |
| 30 | 114–115 | $C_{14}H_{16}ClF_3N_4O_3S$ | C<br>F | 40.73<br>41.05 | 3.91<br>3.74 | 13.57<br>13.46 |
| 31 | 135–137 | $C_{15}H_{18}ClF_3N_4O_3S$ | C<br>F | 42.21<br>42.02 | 4.25<br>4.28 | 13.13<br>12.95 |
| 32 | 125–126 | $C_{15}H_{18}ClF_3N_4O_3S$ | C<br>F | 42.21<br>43.05 | 4.25<br>4.30 | 12.12<br>12.81 |
| 33 | 126–127 | $C_{14}H_{16}ClF_3N_4O_4S$ | C<br>F | 39.21<br>39.98 | 3.76<br>3.77 | 13.07<br>12.87 |
| 35 | 159–160 | $C_{14}H_{16}Cl_2F_2N_4O_5S_2$ | | | | |
| 36 | 215–216 | $C_{15}H_{20}Cl_2N_4O_7S_3$ | C<br>F | 33.64<br>33.88 | 3.77<br>3.91 | 10.46<br>10.68 |
| 37 | 145–147 | $C_{14}H_{16}F_4N_4O_5S_2$ | C<br>F | 36.52<br>36.48 | 3.50<br>3.53 | 12.17<br>12.04 |
| 38 | 143–144 | $C_{14}H_{16}ClF_3N_4O_5S_2$ | | | | |
| 39 | 173–174.5 | $C_{14}H_{18}BrFN_4O_5S_2$ | C<br>F | 34.64<br>33.72 | 3.74<br>3.57 | 11.54<br>10.64 |
| 40 | 145–146 | $C_{14}H_{16}BrF_3N_4O_5S_2$ | C<br>F | 32.25<br>31.94 | 3.09<br>3.10 | 10.75<br>10.78 |
| 41 | 169–172 | $C_{16}H_{22}F_2N_4O_5S_2$ | | | | |
| 42 | 151–153 | $C_{16}H_{21}BrF_2N_4O_5S_2$ | C<br>F | 36.16<br>35.68 | 3.98<br>3.68 | 10.54<br>10.12 |
| 43 | 168–169 | $C_{16}H_{20}Cl_2F_2N_4O_5S_2$ | C<br>F | 36.86<br>37.01 | 3.87<br>3.90 | 10.75<br>10.94 |
| 44 | 64–67 | $C_{16}H_{20}F_4N_4O_5S_2$ | C<br>F | 39.34<br>39.27 | 4.13<br>4.05 | 11.47<br>11.27 |
| 45 | 119–121 | $C_{16}H_{20}ClF_3N_4O_5S_2$ | C<br>F | 38.06<br>38.11 | 3.99<br>3.97 | 11.10<br>10.89 |
| 46 | 128–129 | $C_{16}H_{20}BrF_3N_4O_5S_2$ | C<br>F | 34.98<br>35.00 | 3.67<br>3.61 | 10.20<br>10.12 |
| 47 | oil | $C_{12}H_{12}ClF_3N_4O_3S$ | | | | |
| 48 | 172–173 | $C_{11}H_7ClF_6N_4O_3S$ | C<br>F | 31.12<br>30.86 | 1.66<br>1.61 | 13.19<br>12.99 |
| 49 | oil | $C_{15}H_{18}ClF_3N_4O_3S$ | | | | |
| 50 | 125–126 | $C_{13}H_{14}Cl_2F_2N_4O_3S$ | C<br>F | 37.60<br>37.78 | 3.40<br>3.34 | 13.49<br>13.23 |
| 51 | oil | $C_{14}H_{16}Cl_2F_2N_4O_3S$ | C<br>F | 39.17<br>39.26 | 3.76<br>3.70 | 13.05<br>12.80 |
| 52 | oil | $C_{15}H_{18}Cl_2F_4O_3S_2$ | C<br>F | 40.64<br>40.36 | 4.09<br>4.32 | 12.64<br>12.34 |
| 93 | 122–124 | $C_{18}H_{16}ClF_3N_4O_3S$ | C<br>F | 46.91<br>46.85 | 3.50<br>3.65 | 12.16<br>11.88 |
| 94 | solid | $C_{18}H_{14}Cl_3F_3N_4O_3S$ | C<br>F | 40.81<br>41.27 | 2.66<br>2.55 | 10.58<br>10.19 |
| 96 | 100–101 | $C_{14}H_{14}ClF_3N_4O_3S$ | C<br>F | 40.93<br>40.69 | 3.43<br>3.48 | 13.63<br>13.53 |

TABLE 3

Preemergence Herbicidal Activity (% Control)

| | Compound No. | | | | | | | | | | | | | | | | |
|---|---|---|---|---|---|---|---|---|---|---|---|---|---|---|---|---|---|
| | 1 | 2 | 3 | 4 | 5 | 6 | 9 | 10 | 11 | 12 | 13 | 14 | 15 | 16 | 17 | 18 |
| | Rate (kg/ha) | | | | | | | | | | | | | | | | |
| Species | 0.5 | 1.0 | 0.25 | 0.25 | 0.5 | 1.0 | 0.5 | 1.0 | 0.25 | 0.25 | 0.25 | 1.0 | 0.5 | 2.0 | 1.0 | 0.25 |
| Cotton | 95 | 100 | 100 | 100 | 95 | 40 | 100 | 90 | 100 | 50 | 95 | 40 | 90 | 90 | 90 | 70 |
| Soybean | 50 | 60 | 50 | 50 | 80 | 60 | 20 | 30 | 40 | 10 | 30 | 40 | 10 | 10 | 30 | 10 |
| Field Corn | 100 | 10 | 95 | 100 | 100 | 70 | 95 | 20 | 95 | 10 | 80 | 80 | 90 | 90 | 40 | 95 |
| Rice | 95 | 10 | 90 | 100 | 100 | 50 | 80 | 10 | 95 | 60 | 90 | 30 | 80 | 80 | 70 | 70 |
| Wheat | 50 | 20 | 90 | 90 | 95 | 30 | 20 | 10 | 30 | 0 | 40 | 30 | 20 | 20 | 20 | 20 |
| Field Bindweed | 100 | 50 | 100 | 100 | 95 | 100 | 100 | 80 | 100 | 60 | 100 | 90 | 90 | 100 | 60 | 100 |
| Morningglory | 95 | 90 | 90 | 95 | 100 | 70 | 95 | 90 | 100 | 70 | 100 | 70 | 100 | 100 | 80 | 70 |
| Velvetleaf | 100 | 100 | 100 | 100 | 100 | 100 | 100 | 100 | 100 | 80 | 100 | 90 | 100 | 100 | 100 | 100 |
| Barnyardgrass | 95 | 80 | 95 | 100 | 100 | 95 | 80 | 70 | 100 | 10 | 100 | 90 | 100 | 95 | 70 | 80 |
| Green Foxtail | 100 | 90 | 90 | 100 | 100 | 100 | 70 | 100 | 100 | 30 | 100 | 90 | 95 | 95 | 30 | 70 |
| Johnsongrass | 95 | 70 | 90 | 95 | 100 | 90 | 80 | 70 | 90 | 50 | 90 | 90 | 90 | 70 | 50 | 70 |

| | Compound No. | | | | | | | | | | | | | | | |
|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 35 |
| | Rate (kg/ha) | | | | | | | | | | | | | | | |
| Species | 0.25 | 0.25 | 0.25 | 0.5 | 0.25 | 0.25 | 0.25 | 0.5 | 1.0 | 0.25 | 0.25 | 0.25 | 0.25 | 0.5 | 0.25 | 1.0 |
| Cotton | 80 | 95 | 95 | 95 | 95 | 100 | 95 | 95 | 40 | 100 | 90 | 100 | 90 | 100 | 100 | 100 |
| Soybean | 30 | 95 | 100 | 70 | 30 | 90 | 100 | 100 | 80 | 90 | 90 | 100 | 100 | 95 | 100 | 80 |
| Field Corn | 95 | 100 | 100 | 90 | 20 | 100 | 95 | 100 | 100 | 100 | 100 | 100 | 100 | 100 | 100 | 100 |
| Rice | 80 | 100 | 100 | 90 | 10 | 100 | 95 | 95 | 20 | 100 | 95 | 95 | 100 | 100 | 100 | 80 |
| Wheat | 10 | 95 | 100 | 80 | 20 | 95 | 95 | 100 | 40 | 95 | 80 | 90 | 100 | 100 | 100 | 95 |
| Field Bindweed | 100 | 100 | 100 | 100 | 30 | 95 | 80 | 100 | 80 | 100 | 100 | 100 | 100 | 100 | 100 | 100 |
| Morningglory | 70 | 100 | 100 | 100 | 70 | 100 | 100 | 95 | 60 | 100 | 100 | 100 | 100 | 100 | 100 | 100 |
| Velvetleaf | 100 | 100 | 100 | 100 | 100 | 100 | 100 | 100 | 90 | 100 | 100 | 100 | 100 | 100 | 100 | 100 |
| Barnyardgrass | 95 | 100 | 100 | 70 | 100 | 100 | 100 | 100 | 80 | 100 | 100 | 100 | 100 | 100 | 100 | 100 |
| Green Foxtail | 95 | 100 | 100 | 40 | 100 | 100 | 100 | 100 | 100 | 100 | 100 | 100 | 100 | 100 | 100 | 100 |
| Johnsongrass | 70 | 100 | 100 | 100 | 60 | 100 | 100 | 100 | 90 | 100 | 100 | 100 | 100 | 100 | 100 | 100 |

| | Compound No. | | | | | | | | | | | | | | | |
|---|---|---|---|---|---|---|---|---|---|---|---|---|---|---|---|---|
| | 36 | 37 | 38 | 39 | 40 | 41 | 42 | 43 | 44 | 45 | 46 | 47 | 48 | 49 | 93 | 94 | 96 |
| | Rate (kg/ha) | | | | | | | | | | | | | | | |
| Species | 4.0 | 0.25 | 1.0 | 0.25 | 1.0 | 1.0 | 0.25 | 0.5 | 0.25 | 0.25 | 0.25 | 0.25 | 2.0 | 0.25 | 2.0 | 2.0 | 0.25 |
| Cotton | 0 | 80 | 100 | 40 | 100 | 30 | 80 | 10 | 0 | 30 | 30 | 95 | 100 | 80 | 95 | 80 | 95 |
| Soybean | 0 | 40 | 100 | 20 | 90 | 40 | 80 | 10 | 0 | 30 | 80 | 95 | 20 | 100 | 80 | 10 | 95 |
| Field Corn | 0 | 90 | 100 | 50 | 95 | 100 | 100 | 70 | 95 | 100 | 100 | 95 | 60 | 100 | 100 | 90 | 95 |

TABLE 3-continued

| Preemergence Herbicidal Activity (% Control) | | | | | | | | | | | | | | | | | |
|---|---|---|---|---|---|---|---|---|---|---|---|---|---|---|---|---|---|
| Rice | 10 | 50 | 100 | 20 | 95 | 40 | 80 | 20 | 60 | 80 | 50 | 95 | 80 | 95 | 95 | 50 | 95 |
| Wheat | 0 | 80 | 100 | 10 | 100 | 40 | 30 | — | — | — | — | — | — | — | 100 | 50 | 95 |
| Field Bindweed | 0 | 70 | 100 | 40 | 100 | 90 | 70 | 30 | 60 | 50 | 90 | 100 | 100 | 100 | — | — | — |
| Morningglory | 0 | 90 | 100 | 60 | 100 | 80 | 100 | 50 | 60 | 80 | 95 | 100 | 100 | 100 | 100 | 90 | 100 |
| Velvetleaf | 0 | 100 | 100 | 95 | 100 | 90 | 100 | 20 | 100 | 100 | 100 | 100 | 100 | 100 | 100 | 100 | 100 |
| Barnyardgrass | 10 | 95 | 100 | 30 | 100 | 100 | 95 | 80 | 90 | 100 | 90 | 100 | 100 | 100 | 100 | 95 | 100 |
| Green Foxtail | 20 | 100 | 100 | 30 | 100 | 100 | 90 | 90 | 90 | 95 | 100 | 100 | 100 | 100 | 100 | 95 | 100 |
| Johnsongrass | 20 | 95 | 100 | 90 | 100 | 95 | 95 | 70 | 90 | 95 | 100 | 100 | 100 | 100 | 100 | 95 | 100 |

TABLE 4

| Postemergence Herbicidal Activity (% Control) | | | | | | | | | | | | | | | | | |
|---|---|---|---|---|---|---|---|---|---|---|---|---|---|---|---|---|---|
| Compound No. | 1 | 2 | 3 | 4 | 5 | 6 | 9 | 10 | 11 | 12 | 13 | 14 | 15 | 16 | 17 | 18 | 19 |
| Species / Rate (kg/ha) | 0.5 | 1.0 | 0.25 | 0.25 | 0.5 | 1.0 | 0.5 | 1.0 | 0.25 | 0.25 | 0.25 | 1.0 | 0.5 | 2.0 | 1.0 | 0.25 | 0.25 |
| Cotton | 100 | 100 | 100 | 100 | 100 | 80 | 100 | 100 | 100 | 30 | 90 | 70 | 100 | 100 | 60 | 60 | 100 |
| Soybean | 60 | 80 | 60 | 80 | 80 | 60 | 40 | 70 | 80 | 40 | 70 | 50 | 70 | 40 | 40 | 50 | 70 |
| Field Corn | 40 | 30 | 70 | 80 | 70 | 50 | 40 | 30 | 60 | 20 | 90 | 30 | 70 | 100 | 20 | 40 | 80 |
| Rice | 95 | 20 | 90 | 95 | 80 | 50 | 90 | 20 | 90 | 40 | 80 | 20 | 50 | 80 | 30 | 80 | 70 |
| Wheat | 80 | 40 | 50 | 70 | 80 | 40 | 80 | 40 | 50 | 10 | 30 | 30 | 100 | 40 | 30 | 30 | 30 |
| Field Bindweed | 100 | 60 | 80 | 95 | 100 | 50 | 100 | 40 | 100 | 10 | 100 | 70 | 80 | 100 | 50 | 80 | 90 |
| Morningglory | 100 | 95 | 100 | 95 | 95 | 95 | 100 | 90 | 95 | 30 | 100 | 90 | 90 | 100 | 80 | 70 | 90 |
| Velvetleaf | 100 | 100 | 100 | 80 | 100 | 80 | 100 | 100 | 100 | 10 | 100 | 50 | 100 | 100 | 70 | 100 | 100 |
| Barnyardgrass | 100 | 50 | 100 | 95 | 100 | 50 | 95 | 50 | 80 | 40 | 95 | 50 | 80 | 100 | 40 | 70 | 90 |
| Green Foxtail | 95 | 70 | 100 | 80 | 100 | 80 | 100 | 40 | 80 | 40 | 95 | 90 | 40 | 95 | 40 | 95 | 70 |
| Johnsongrass | 100 | 40 | 70 | 70 | 90 | 50 | 95 | 30 | 70 | 30 | 60 | 80 | 90 | 80 | 30 | 30 | 60 |
| Compound No. | 20 | 21 | 22 | 23 | 24 | 25 | 26 | 27 | 28 | 29 | 30 | 31 | 32 | 33 | 35 | 36 | |
| Species / Rate (kg/ha) | 0.25 | 0.25 | 0.5 | 0.25 | 0.25 | 0.25 | 0.5 | 1.0 | 0.25 | 0.25 | 0.25 | 0.25 | 0.5 | 0.25 | 1.0 | 4.0 | |
| Cotton | 100 | 100 | 100 | 40 | 100 | 100 | 100 | 40 | 100 | 95 | 100 | 95 | 100 | 100 | 80 | 20 | |
| Soybean | 95 | 100 | 50 | 40 | 90 | 95 | 95 | 60 | 95 | 95 | 100 | 100 | 100 | 100 | 60 | 10 | |
| Field Corn | 100 | 100 | 70 | 20 | 90 | 95 | 80 | 70 | 80 | 80 | 90 | 100 | 100 | 100 | 100 | 10 | |
| Rice | 100 | 100 | 90 | 0 | 80 | 95 | 50 | 20 | 40 | 40 | 90 | 95 | 100 | 100 | 80 | 10 | |
| Wheat | 80 | 100 | 40 | 20 | 70 | 95 | 80 | 50 | 70 | 70 | 90 | 100 | 100 | 100 | 60 | 0 | |
| Field Bindweed | 100 | 100 | 100 | 20 | 95 | 100 | 95 | 30 | 90 | 30 | 95 | 100 | 100 | 90 | 90 | 20 | |
| Morningglory | 100 | 100 | 100 | 20 | 95 | 100 | 100 | 70 | 95 | 90 | 100 | 100 | 100 | 100 | 100 | 0 | |
| Velvetleaf | 100 | 100 | 100 | 30 | 100 | 100 | 100 | 20 | 100 | 70 | 100 | 100 | 100 | 100 | 90 | 0 | |
| Barnyardgrass | 100 | 100 | 100 | 20 | 90 | 100 | 100 | 70 | 95 | 70 | 95 | 100 | 100 | 100 | 100 | 20 | |
| Green Foxtail | — | — | 100 | 20 | 95 | 100 | 100 | 100 | 95 | 95 | 95 | 100 | 100 | 100 | 100 | 30 | |
| Johnsongrass | 90 | 100 | 100 | 20 | 95 | 100 | 100 | 70 | 80 | 80 | 90 | 100 | 100 | 90 | 100 | 20 | |
| Compound No. | 37 | 38 | 39 | 40 | 41 | 42 | 43 | 44 | 45 | 46 | 47 | 48 | 49 | 93 | 94 | 96 | |
| Species / Rate (kg/ha) | 0.25 | 1.0 | 0.25 | 1.0 | 1.0 | 0.25 | 1.0 | 1.0 | 1.0 | 0.25 | 0.25 | 2.0 | 0.25 | 0.25 | 2.0 | 0.25 | |
| Cotton | 40 | 100 | 40 | 100 | 40 | 95 | 95 | 40 | 90 | 100 | 100 | 100 | 90 | 100 | 100 | 100 | |
| Soybean | 40 | 100 | 40 | 90 | 60 | 90 | 40 | 40 | 80 | 80 | 95 | 95 | 100 | 95 | 50 | 95 | |
| Field Corn | 70 | 100 | 10 | 100 | 80 | 80 | 60 | 40 | 100 | 95 | 80 | 100 | 100 | 100 | 50 | 100 | |
| Rice | 30 | 100 | 20 | 100 | 40 | 30 | 20 | 20 | 80 | 20 | 80 | 50 | 95 | 70 | 20 | 100 | |
| Wheat | 30 | 100 | 20 | 100 | 50 | 40 | 10 | 40 | 80 | 60 | 90 | 50 | 100 | 95 | 40 | 100 | |
| Field Bindweed | 30 | 100 | 30 | 100 | 30 | 40 | 0 | 50 | 95 | 100 | 100 | 100 | 100 | — | — | — | |
| Morningglory | 80 | 100 | 90 | 100 | 50 | 60 | 90 | 50 | 95 | 100 | 100 | 100 | 100 | 80 | 40 | 100 | |
| Velvetleaf | 100 | 100 | 60 | 100 | 30 | 100 | 40 | 40 | 100 | 100 | 100 | 100 | 100 | 90 | 85 | 100 | |
| Barnyardgrass | 60 | 100 | 20 | 100 | 95 | 70 | 60 | 40 | 100 | 100 | 95 | 95 | 100 | 100 | 70 | 100 | |
| Green Foxtail | 50 | 100 | 70 | 100 | 80 | 50 | 90 | 60 | 95 | 100 | 95 | 95 | 100 | 80 | 60 | 100 | |
| Johnsongrass | 50 | 100 | 30 | 100 | 95 | 80 | 30 | 40 | 95 | 90 | 95 | 80 | 100 | 70 | 50 | 95 | |

I claim:
1. A compound of the formula

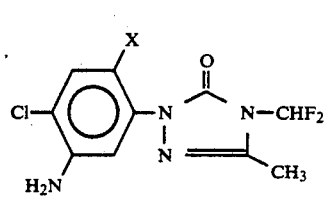

in which X is F or Cl.

2. The compound of claim 1 in which X is Cl.

* * * * *